US008602286B2

(12) United States Patent
Crainich et al.

(10) Patent No.: US 8,602,286 B2
(45) Date of Patent: Dec. 10, 2013

(54) APPARATUS FOR FEEDING STAPLES IN A LOW PROFILE SURGICAL STAPLER

(75) Inventors: Lawrence Crainich, Charlestown, NH (US); Jason L. Harris, Mason, OH (US); Michael J. Stokes, Cincinnati, OH (US); Matthew D. Holcomb, Lebanon, OH (US); Jonathan B. O'Keefe, North Attleboro, MA (US); Keith D. Boudreau, Beverly, MA (US); Jeffrey C. Cerier, Franklin, MA (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 436 days.

(21) Appl. No.: 12/690,285

(22) Filed: Jan. 20, 2010

(65) Prior Publication Data

US 2010/0187284 A1 Jul. 29, 2010

Related U.S. Application Data

(63) Continuation of application No. 12/608,860, filed on Oct. 29, 2009, and a continuation of application No. 12/609,336, filed on Oct. 30, 2009, now abandoned.

(51) Int. Cl.
*A61B 17/068* (2006.01)
(52) U.S. Cl.
USPC .................. 227/175.1; 227/179.1; 227/181.1
(58) Field of Classification Search
USPC ........... 227/175.1, 179.1, 181.1; 606/75, 151, 606/219, 139–143, 157
See application file for complete search history.

(56) References Cited

U.S. PATENT DOCUMENTS

| | | | |
|---|---|---|---|
| 2,185,518 A | 1/1940 | Posnack | |
| 3,638,847 A | 2/1972 | Noiles et al. | |
| 3,740,994 A | 6/1973 | De Carlo, Jr. | |
| 3,819,100 A * | 6/1974 | Noiles et al. | 227/19 |
| 4,086,926 A | 5/1978 | Green et al. | |
| 4,396,139 A | 8/1983 | Hall et al. | |
| 4,407,286 A | 10/1983 | Noiles et al. | |

(Continued)

FOREIGN PATENT DOCUMENTS

| | | |
|---|---|---|
| DE | 29720952 U1 | 1/1998 |
| EP | 0068046 B1 | 5/1988 |

(Continued)

OTHER PUBLICATIONS

Talebpour M, Amoli BS. Laparoscopic total gastric vertical plication in morbid obesity. J Laparoendosc Adv Surg Tech A 2007;17:793-8.

(Continued)

*Primary Examiner* — Alexandra Elve
*Assistant Examiner* — Nathaniel Chukwurah

(57) ABSTRACT

A mechanism for feeding a fastener including a housing having a longitudinal axis and at least one fastener within the housing. The fastener has a crown and at least two legs extending therefrom. The fastener is disposed within the housing in a first plane parallel to the longitudinal axis. The mechanism includes an elongated actuator disposed within the housing. The actuator has a shaft substantially parallel to the longitudinal axis of the mechanism and rigidly spaced from the fastener in a second plane. The actuator has at least one radially extending advancer disposed along a length thereof, and a mechanism for rotating the actuator so that the advancer engages the fastener.

4 Claims, 28 Drawing Sheets

(56) References Cited

U.S. PATENT DOCUMENTS

| | | | |
|---|---|---|---|
| 4,489,875 A | 12/1984 | Crawford et al. | |
| 4,505,273 A | 3/1985 | Braun et al. | |
| 4,509,518 A | 4/1985 | McGarry et al. | |
| 4,624,254 A | 11/1986 | McGarry et al. | |
| 4,648,542 A | 3/1987 | Fox et al. | |
| 4,669,647 A | 6/1987 | Storace | |
| 4,874,122 A | 10/1989 | Froelich et al. | |
| 4,899,745 A | 2/1990 | Laboureau et al. | |
| 5,032,127 A | 7/1991 | Frazee et al. | |
| 5,156,609 A | 10/1992 | Nakao et al. | |
| 5,242,457 A * | 9/1993 | Akopov et al. | 606/144 |
| 5,333,772 A | 8/1994 | Rothfuss et al. | |
| 5,350,400 A | 9/1994 | Esposito et al. | |
| 5,392,978 A | 2/1995 | Velez et al. | |
| 5,413,584 A | 5/1995 | Schulze | |
| 5,439,468 A | 8/1995 | Schulze et al. | |
| 5,544,802 A | 8/1996 | Crainich | |
| 5,626,585 A | 5/1997 | Mittelstadt et al. | |
| 5,645,567 A | 7/1997 | Crainich | |
| 5,715,987 A | 2/1998 | Kelley et al. | |
| 5,725,554 A | 3/1998 | Simon et al. | |
| 5,732,871 A | 3/1998 | Clark et al. | |
| 5,829,662 A | 11/1998 | Allen et al. | |
| 6,228,098 B1 | 5/2001 | Kayan et al. | |
| 6,277,131 B1 | 8/2001 | Kalikow | |
| 6,306,149 B1 | 10/2001 | Meade | |
| 6,330,964 B1 | 12/2001 | Kayan et al. | |
| 6,352,541 B1 | 3/2002 | Kienzle et al. | |
| 6,450,391 B1 | 9/2002 | Kayan et al. | |
| 6,530,933 B1 | 3/2003 | Yeung et al. | |
| 6,695,854 B1 | 2/2004 | Kayan et al. | |
| 6,767,356 B2 | 7/2004 | Kanner et al. | |
| 6,837,895 B2 * | 1/2005 | Mayenberger | 606/142 |
| 6,915,937 B2 | 7/2005 | Lat et al. | |
| 6,957,756 B2 | 10/2005 | Lat et al. | |
| 7,056,330 B2 | 6/2006 | Gayton | |
| 7,059,509 B2 | 6/2006 | Brown | |
| 7,112,214 B2 | 9/2006 | Peterson et al. | |
| 7,179,265 B2 | 2/2007 | Manetakis et al. | |
| 7,320,692 B1 | 1/2008 | Bender et al. | |
| 7,344,544 B2 | 3/2008 | Bender et al. | |
| 7,458,978 B1 | 12/2008 | Bender et al. | |
| 7,473,258 B2 | 1/2009 | Clauson et al. | |
| 7,753,870 B2 | 7/2010 | Demarais et al. | |
| 2004/0225305 A1 | 11/2004 | Ewers et al. | |
| 2005/0080454 A1 | 4/2005 | Drews et al. | |
| 2005/0085830 A1 | 4/2005 | Lehman et al. | |
| 2006/0020276 A1 | 1/2006 | Saadat et al. | |
| 2007/0185504 A1 | 8/2007 | Manetakis et al. | |
| 2008/0249566 A1 | 10/2008 | Harris et al. | |
| 2008/0319455 A1 | 12/2008 | Harris et al. | |
| 2009/0072006 A1 | 3/2009 | Clauson et al. | |
| 2009/0112233 A1 | 4/2009 | Xiao | |
| 2009/0134198 A1 | 5/2009 | Knodel et al. | |
| 2009/0206127 A1 | 8/2009 | Danielson et al. | |
| 2009/0318936 A1 | 12/2009 | Harris et al. | |
| 2010/0187283 A1 | 7/2010 | Crainich et al. | |
| 2010/0191255 A1 | 7/2010 | Crainich et al. | |

FOREIGN PATENT DOCUMENTS

| | | |
|---|---|---|
| EP | 0864297 B1 | 6/2007 |
| EP | 1908423 B1 | 1/2011 |
| WO | 01/76489 A1 | 10/2001 |
| WO | 2008/109876 A1 | 9/2008 |
| WO | WO 2008/112942 | 9/2008 |
| WO | 2008/118928 A2 | 10/2008 |
| WO | 2009/137517 A1 | 11/2009 |
| WO | 2012/103286 A1 | 8/2012 |
| WO | 2012/103291 A1 | 8/2012 |

OTHER PUBLICATIONS

Sales Puccini, CE. Surset gástrico de Sales: una alternative para cirugia bariátrica restrictive. Rev Colomb Cir 2008;23(3):131-5.

Fusco PEB, Poggetti RS, Younes RN, Fontes B, Birolini D. Evaluation of gastric greater curvature invagination for weight loss in rats. Obes Surg 2006;16:171-7.

Fusco PEB, Poggetti RS, Younes RN, Fontes B, Birolini D. Comparison of anterior gastric wall and greater gastric curvature invaginations for weight loss in rats. Obes Surg 2007;17:1340-5.

Brethauer SA, Harris JL, Chand B, Kroh M, Rogula T, Schauer PR. Initial results of vertical gastric plication for severe obesity. Society of American Gastrointestinal and Endoscopic Surgeons. Phoenix, Arizona. Apr. 22-25, 2009.

Ramos AC, Galvao M, Behrens E, Montufar F, Zundel N. Tubular sleeve gastroplasty (TSG) as a new approach to bariatric treatment. 14th World Congress of the International Federation for the Surgery of Obesity—Paris, France—Aug. 26-29, 2009.

International Search Report dated Apr. 5, 2011 (PCT/US2011/020476).

International Search Report dated Apr. 10, 2012 (PCT/US2012/022656).

International Search Report dated Apr. 10, 2012 (PCT/US2012/022651).

European Search Report, dated Oct. 1, 2012, Application No. 12172811.7.

European Search Report, dated Oct. 1, 2012, Application No. 12172808.3.

European Search Report, dated Oct. 1, 2012, Application No. 12172816.6.

Co-pending U.S. Appl. No. 12/359,351, filed Jan. 26, 2009, first named inventor Jason L. Harris.

Co-pending U.S. Appl. No. 12/359,354, filed Jan. 26, 2009, first named inventor Jason L. Harris.

Co-pending U.S. Appl. No. 12/359,357, filed Jan. 26, 2009, first named inventor Jason L. Harris.

Co-pending U.S. Appl. No. 12/608,860, filed Oct. 29, 2009, first named inventor Jason L. Harris.

Co-pending U.S. Appl. No. 12/609,336, filed Oct. 30, 2009, first named inventor Lawrence Crainich.

Co-pending U.S. Appl. No. 13/015,966, filed Jan. 28, 2011, first named inventor Matthew D. Holcomb.

Co-pending U.S. Appl. No. 13/015,977, filed Jan. 28, 2011, first named inventor Matthew D. Holcomb.

Co-pending U.S. Appl. No. 13/164,949, filed Jun. 21, 2011, first named inventor Matthew D. Holcomb.

Co-pending U.S. Appl. No. 13/164,954, filed Jun. 21, 2011, first named inventor Matthew D. Holcomb.

Co-pending U.S. Appl. No. 13/164,960, filed Jun. 21, 2011, first named inventor Matthew D. Holcomb.

Co-pending U.S. Appl. No. 13/164,963, filed Jun. 21, 2011, first named inventor Jason L. Harris.

Co-pending U.S. Appl. No. 13/362,172, filed Jan. 31, 2012, first named inventor Jason L. Harris.

Co-pending U.S. Appl. No. 13/371,678, filed Feb. 13, 2012, first named inventor Matthew D. Holcomb.

Co-pending U.S. Appl. No. 13/371,684, filed Feb. 13, 2012, first named inventor Matthew D. Holcomb.

International Search Report dated Apr. 7, 2011; International Application No. PCT/US2011/020472.

International Search Report dated Jan. 6, 2010; International Application No. PCT/US2010/021929.

International Search Report dated Aug. 13, 2010; International Application No. PCT/US2010/021953.

* cited by examiner

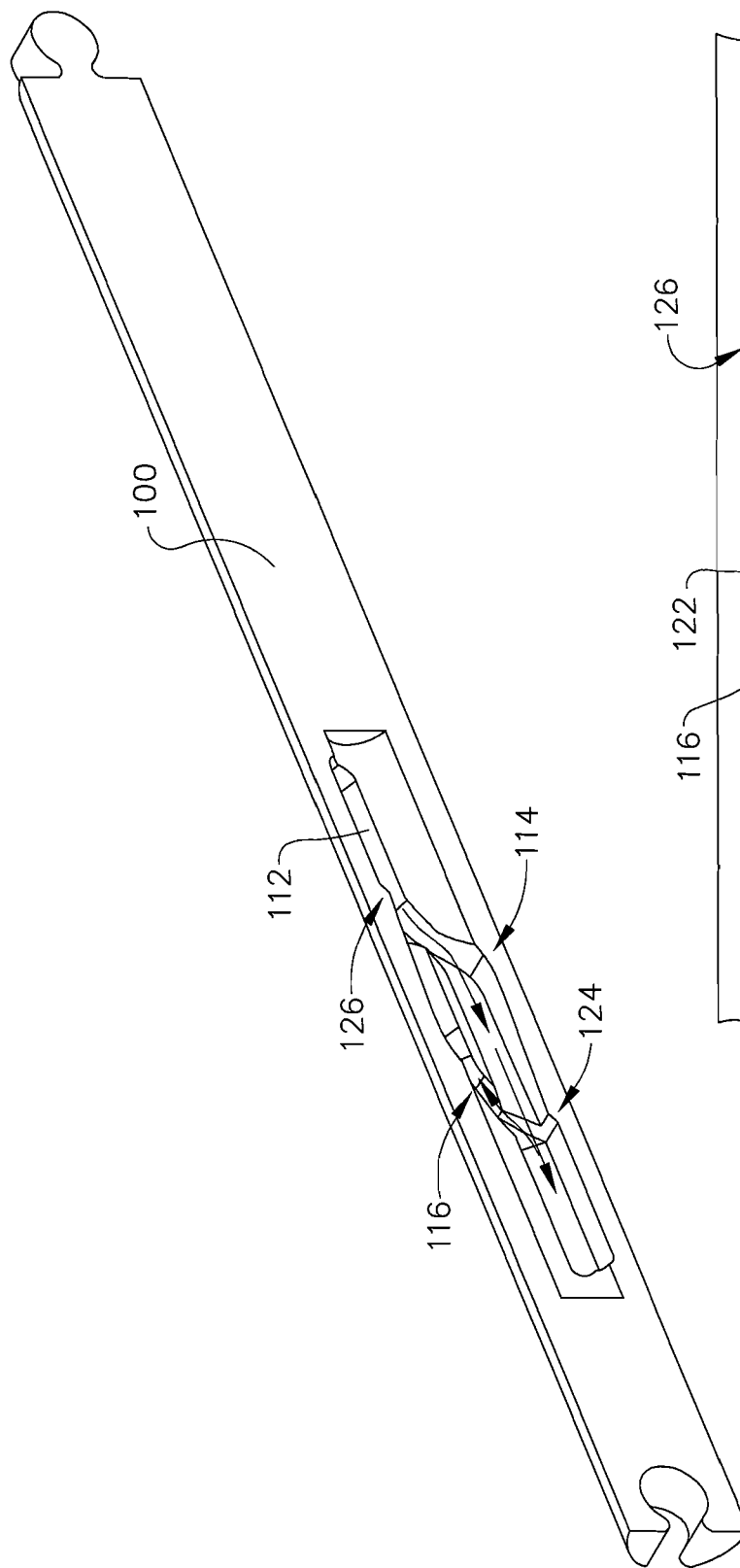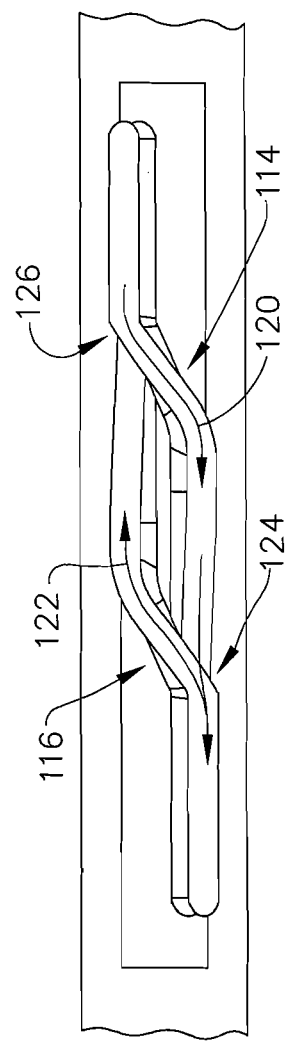

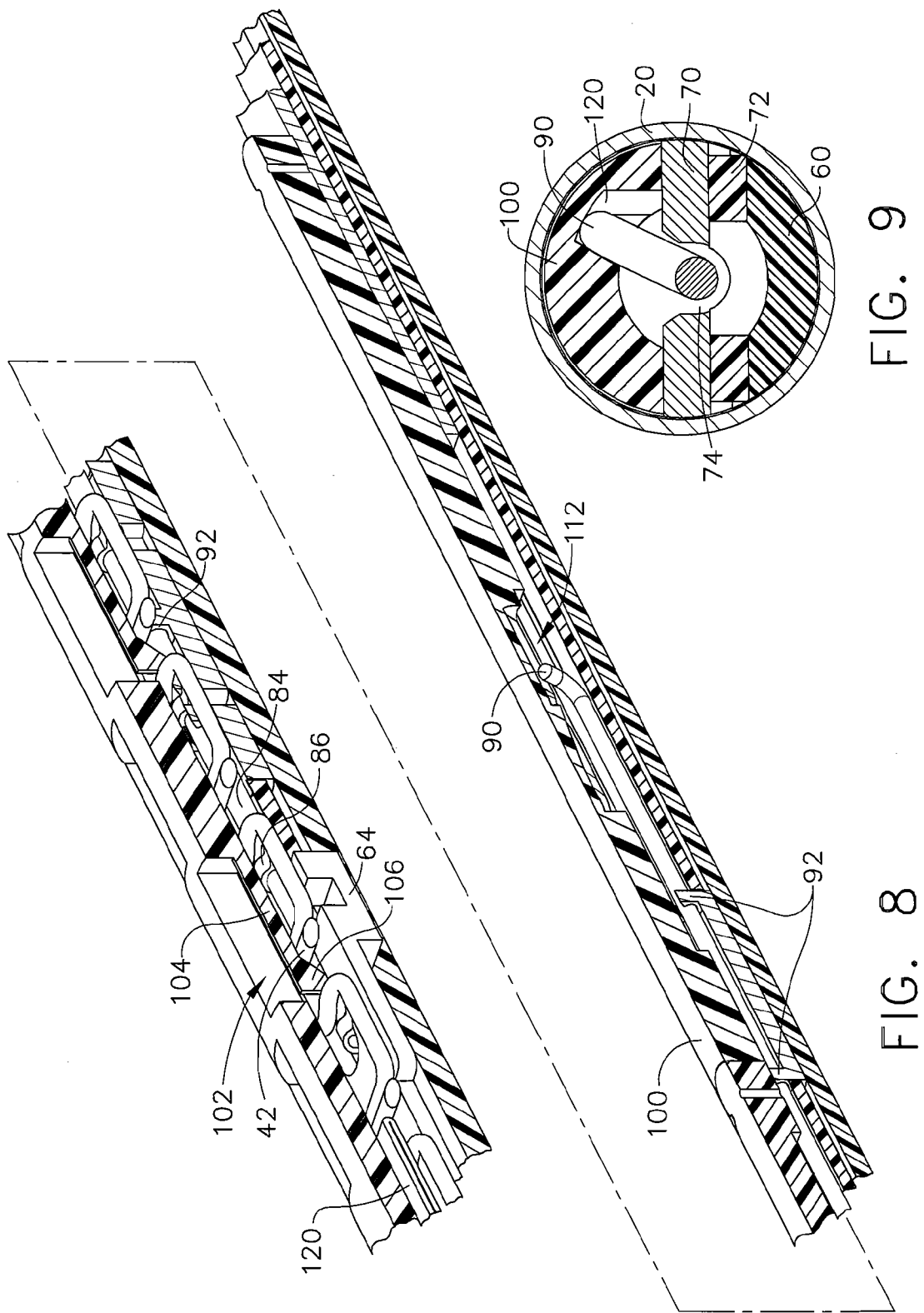

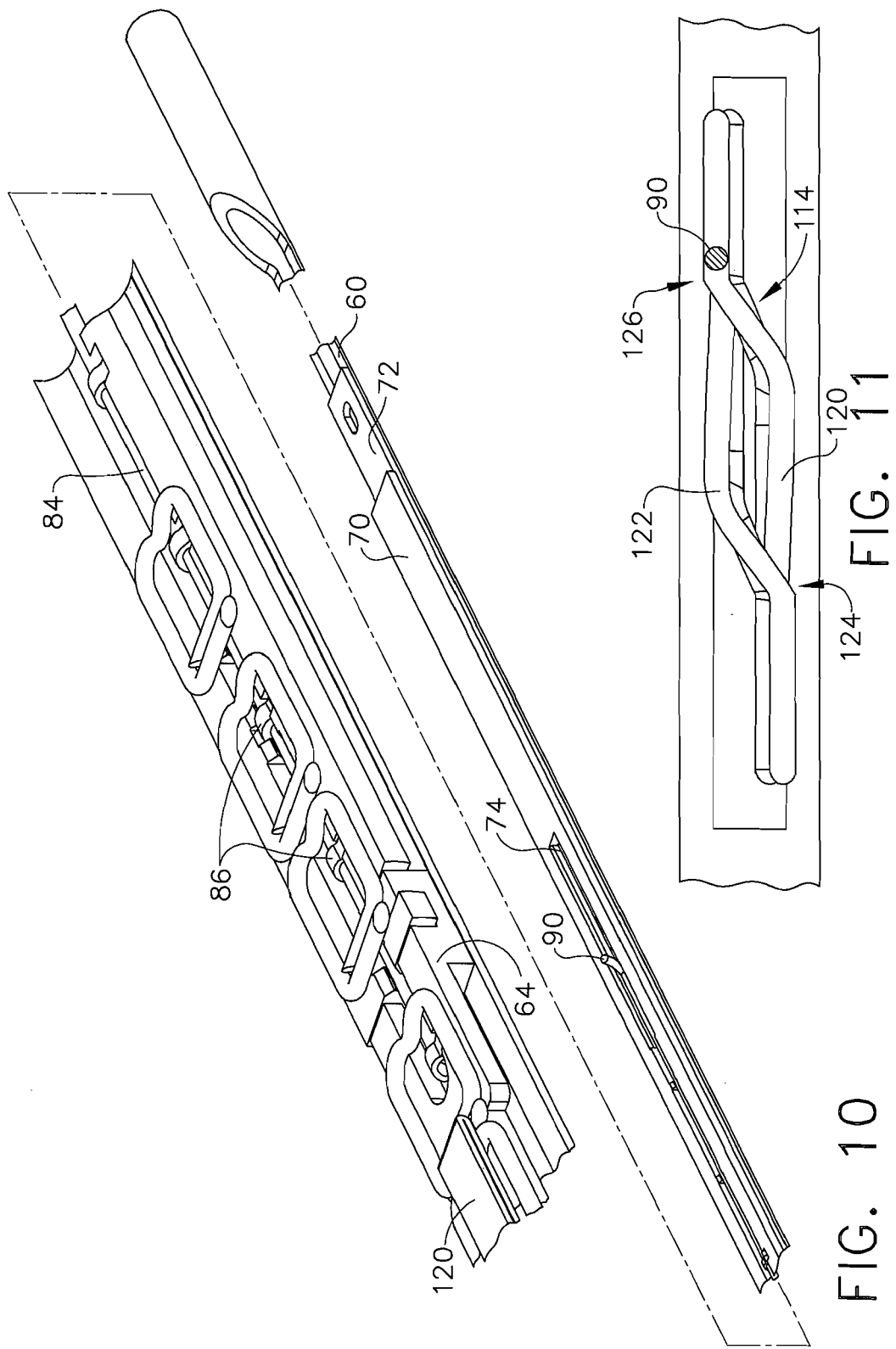

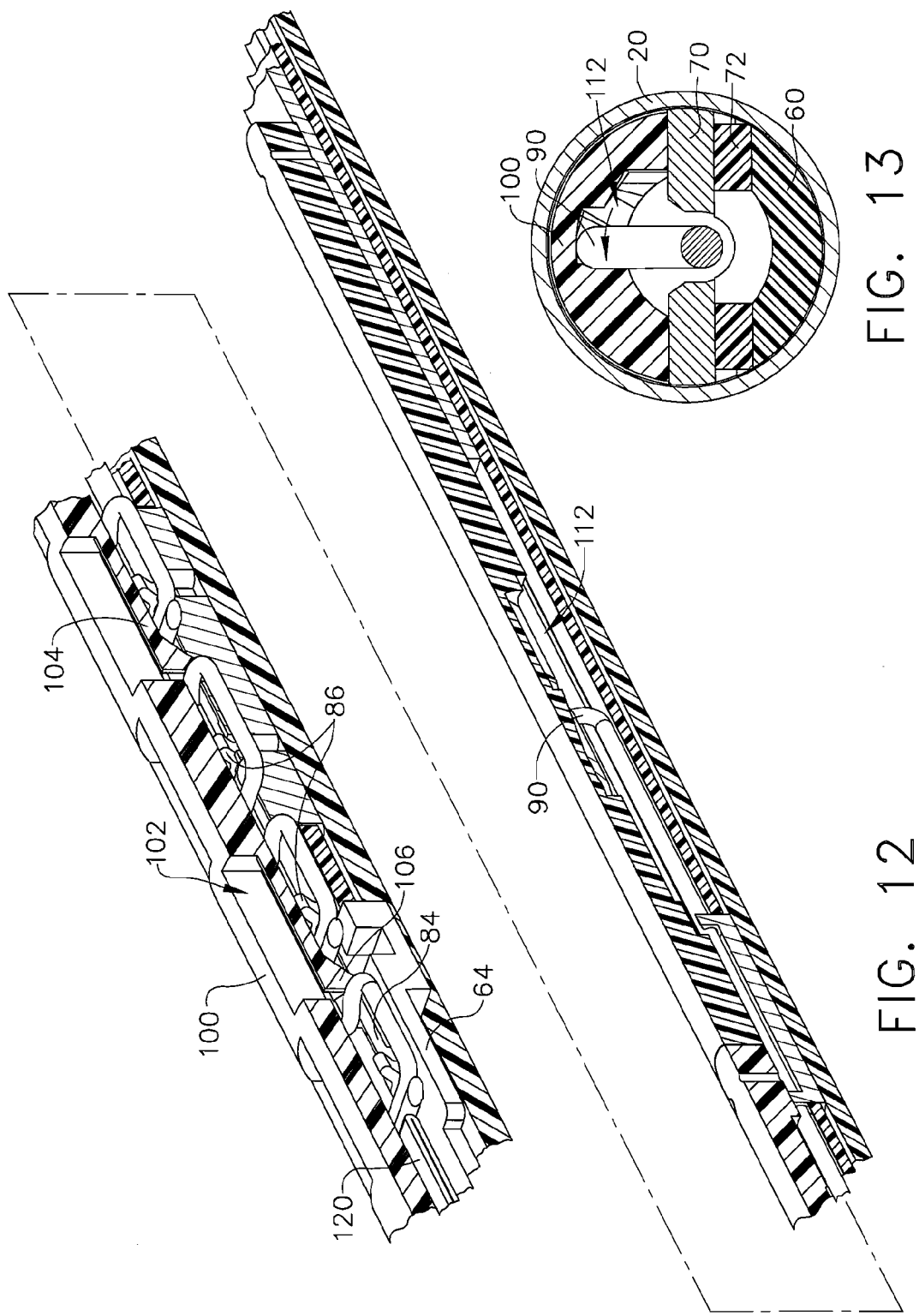

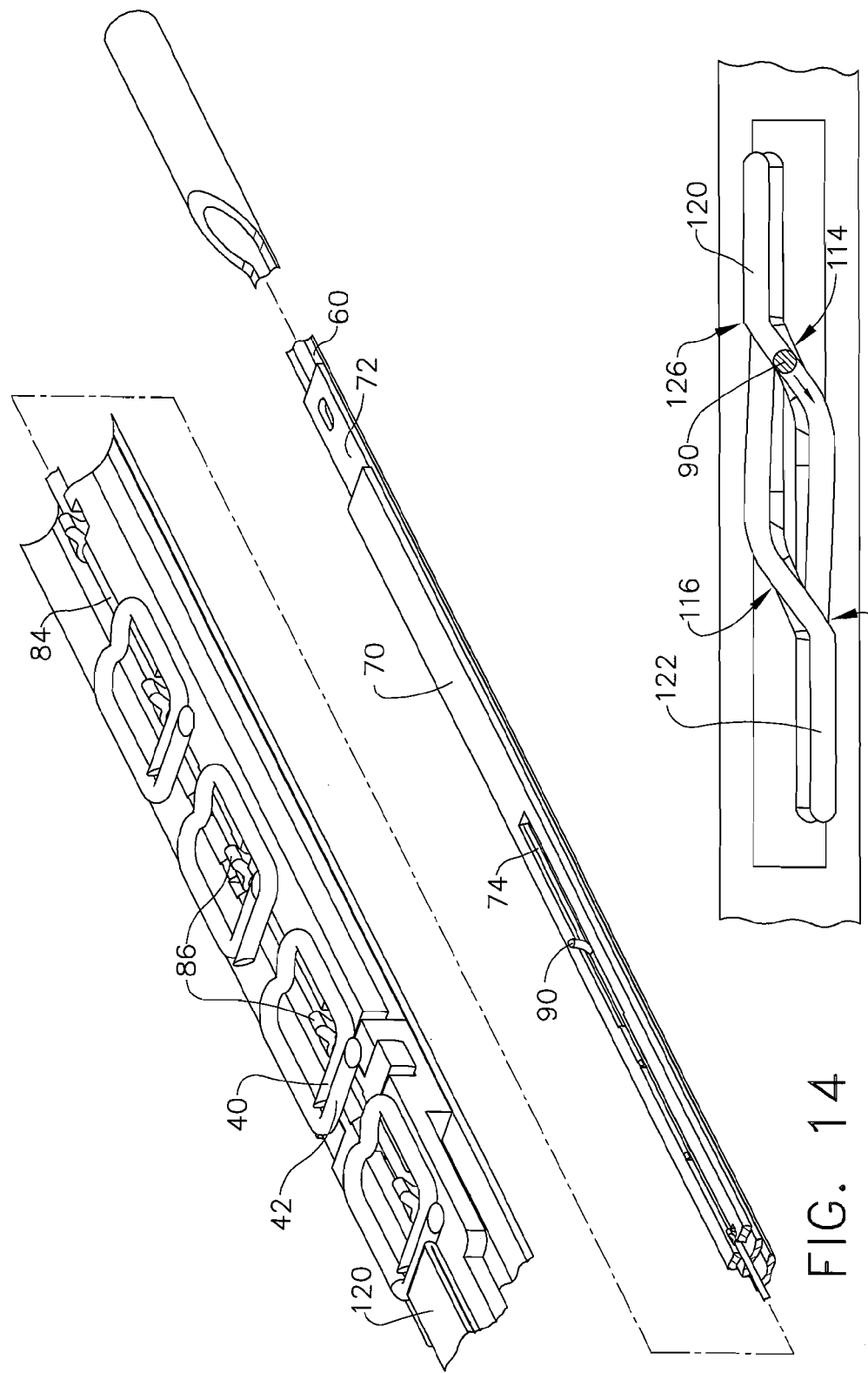

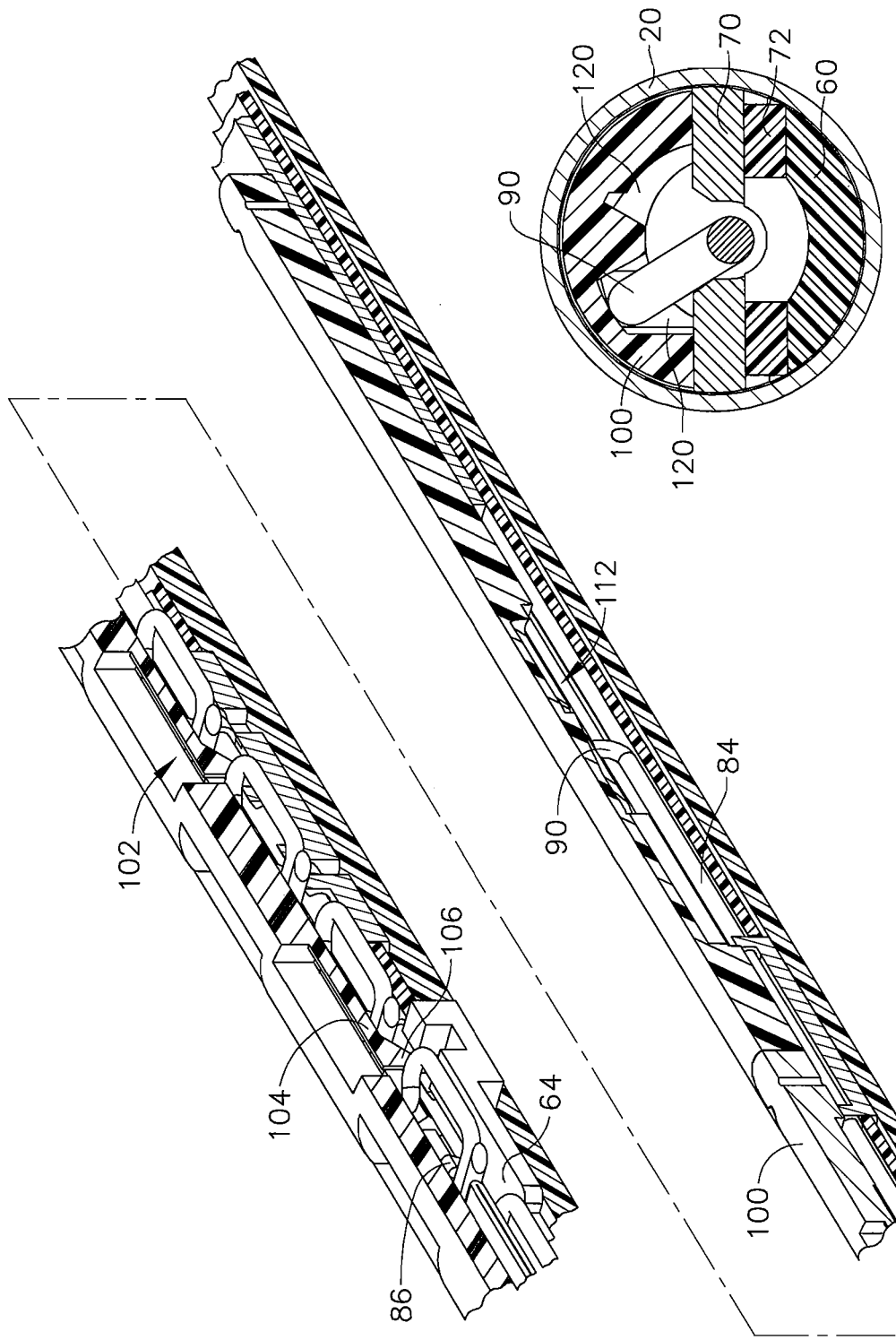

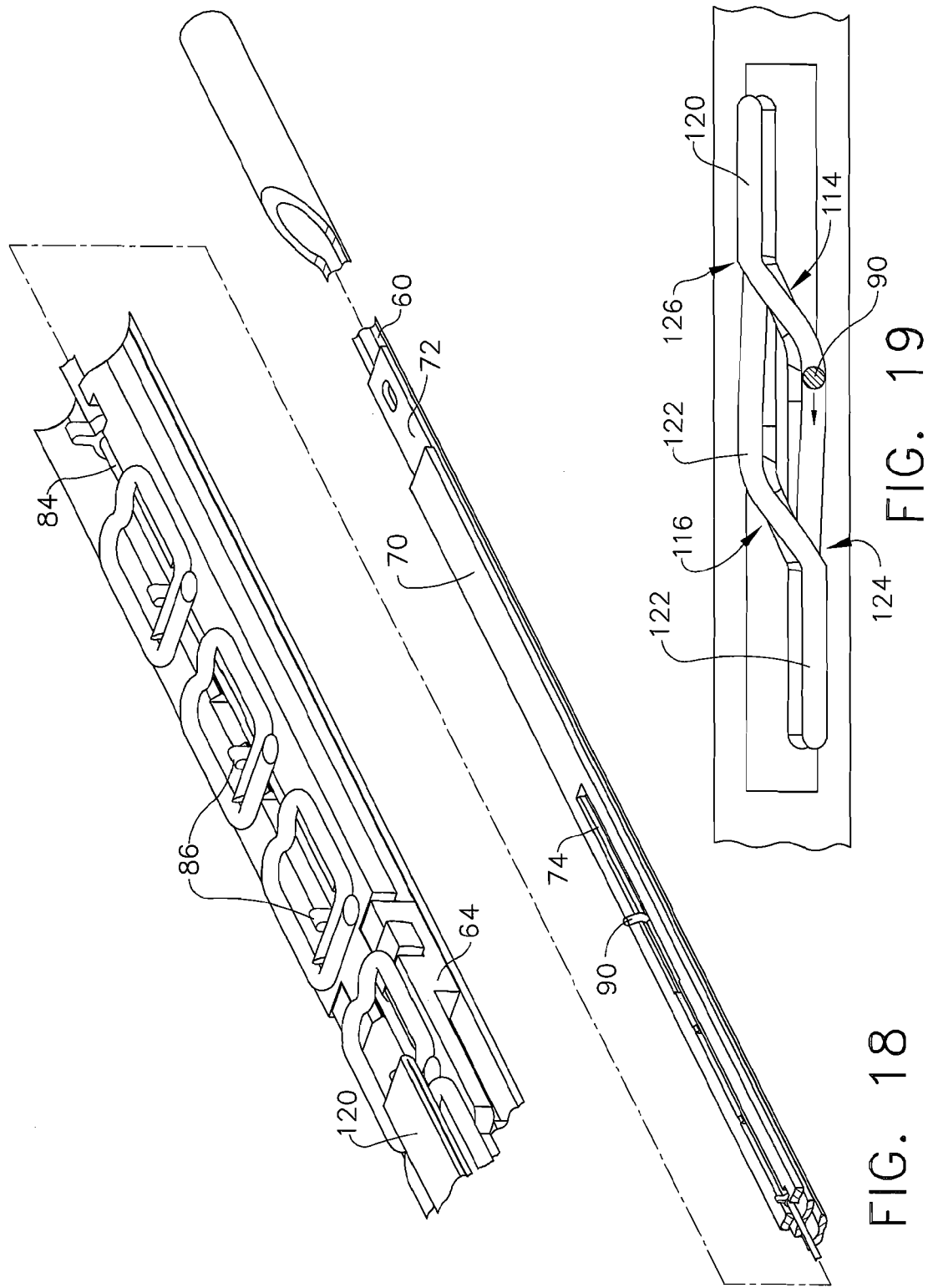

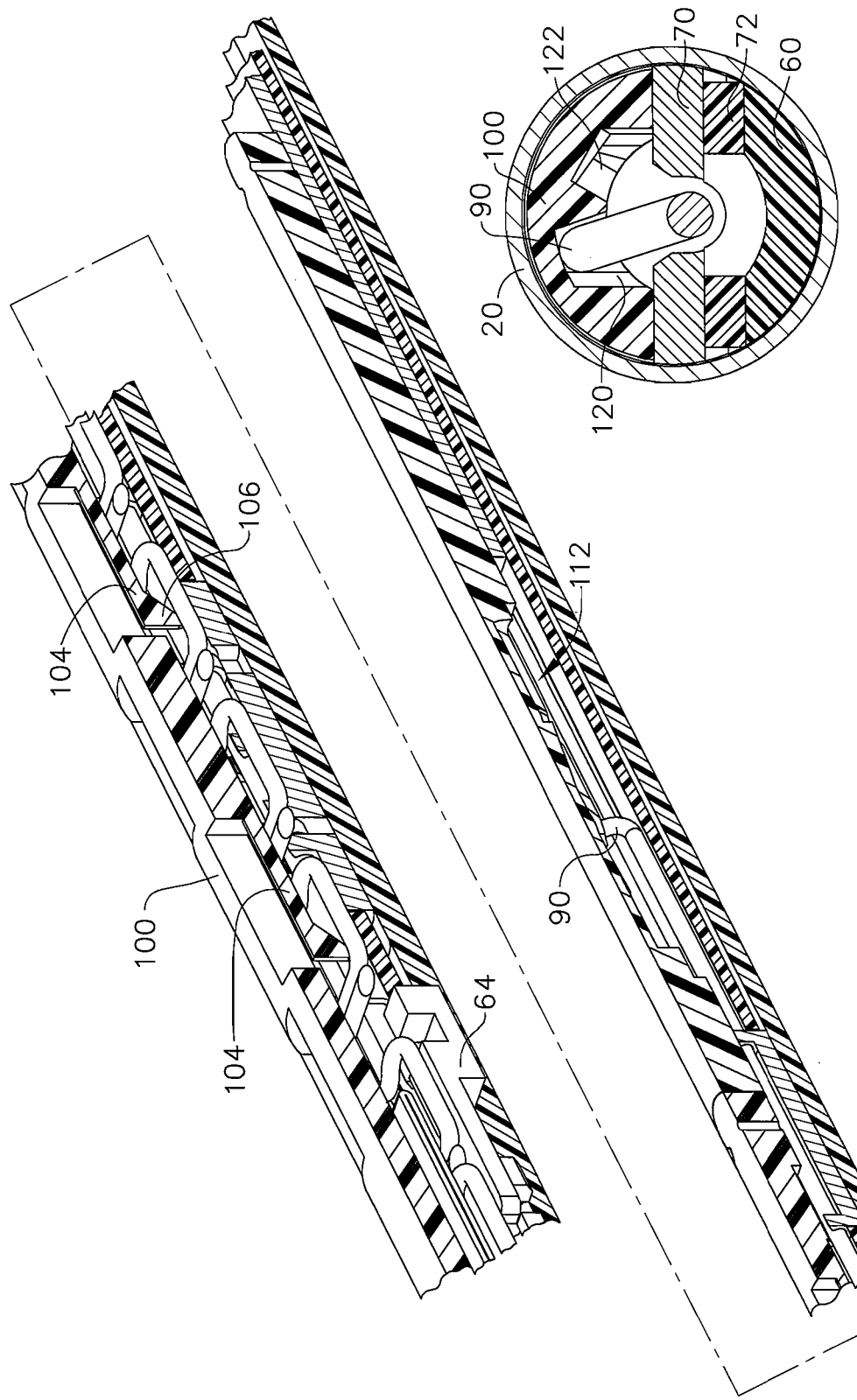

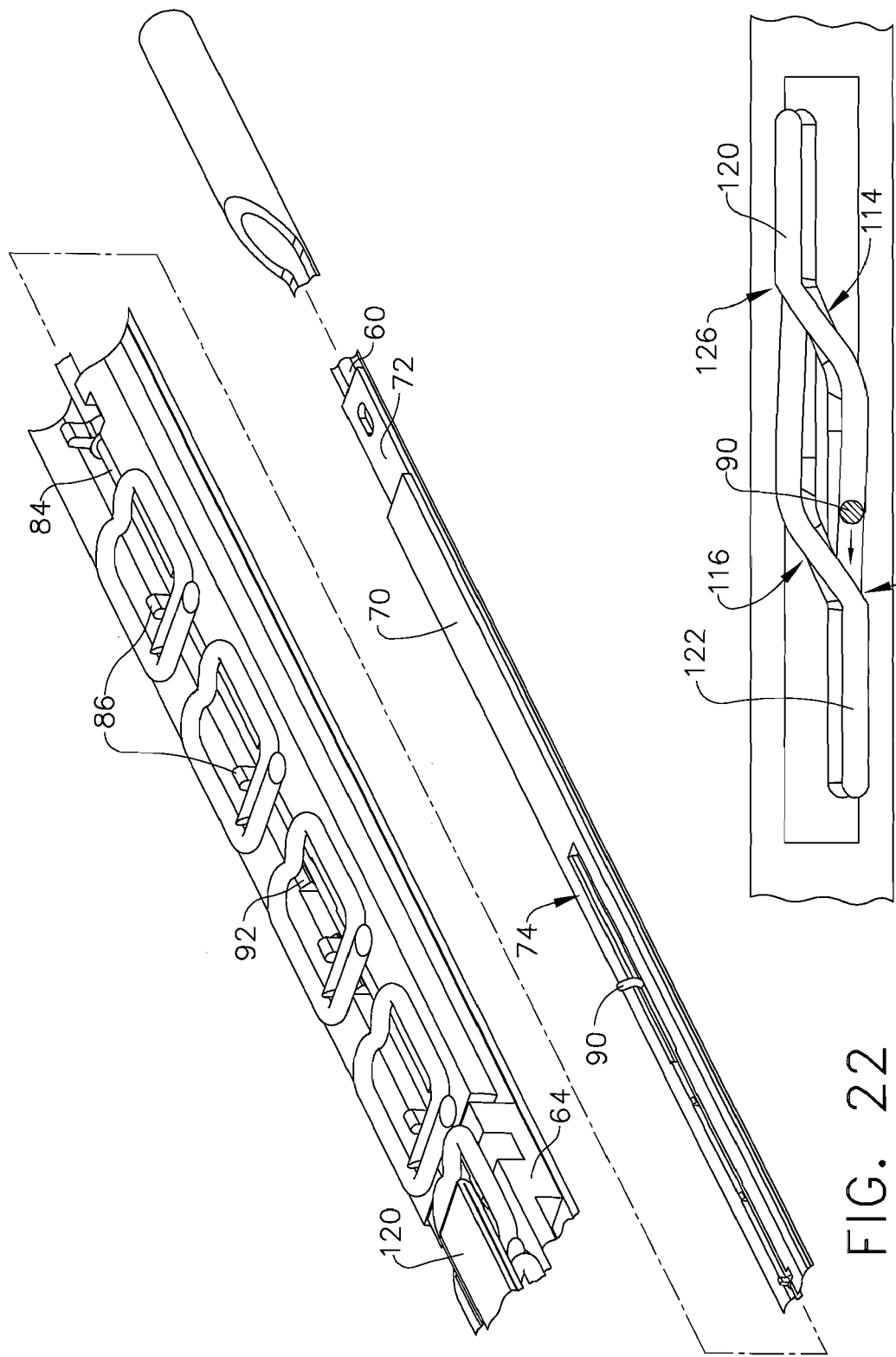

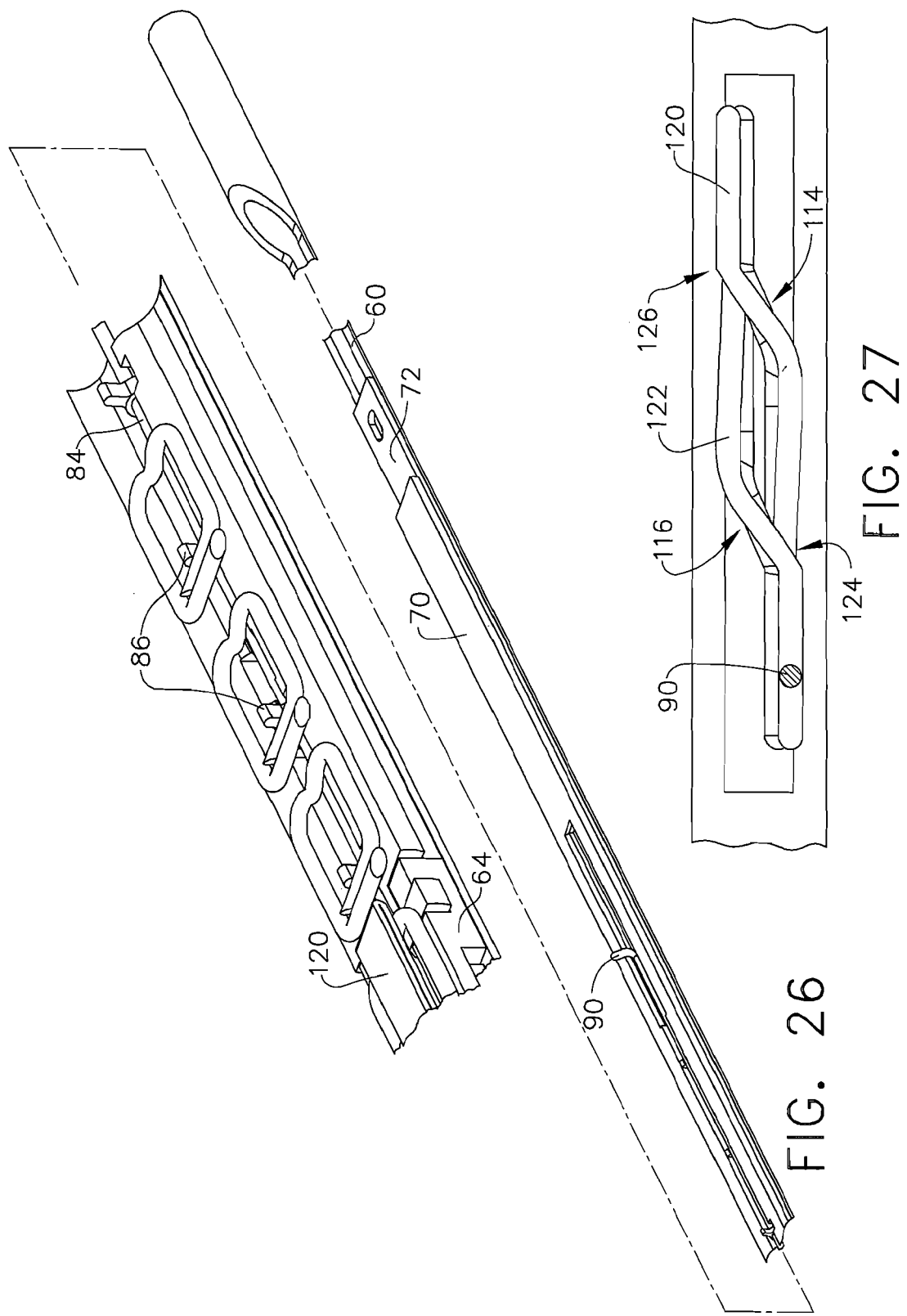

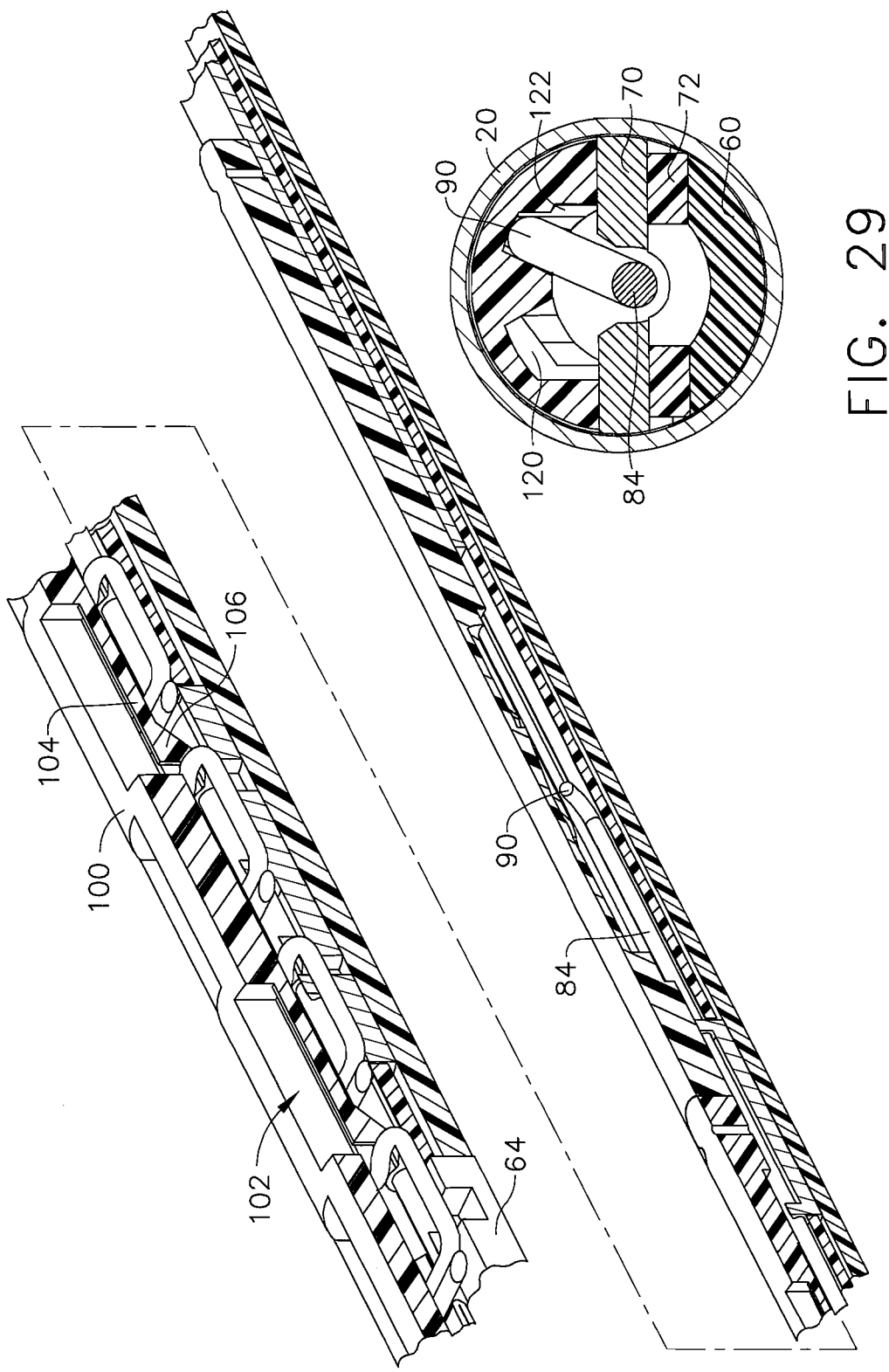

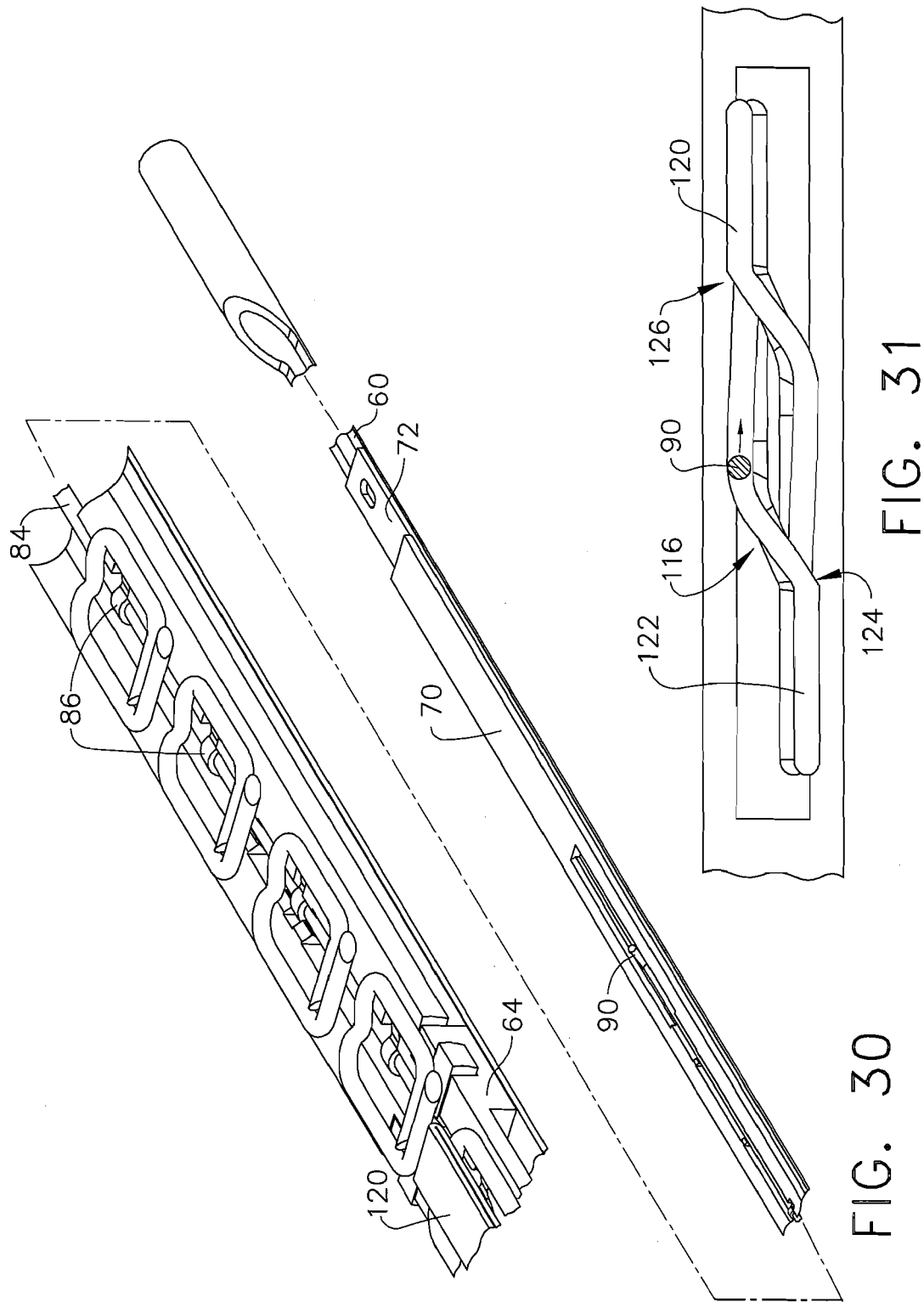

APPARATUS FOR FEEDING STAPLES IN A LOW PROFILE SURGICAL STAPLER

REFERENCE TO RELATED APPLICATIONS

This application is a continuation-in-application of 12/608,860 filed Oct. 29, 2009; 12/609,336 filed Oct. 30, 2009 now abandoned and claims priority of Pending U.S. patent application Ser. No. 12/359,351 filed Jan. 26, 2009; Pending U.S. patent application Ser. No. 12/359,354 filed Jan. 26, 2009 and Pending U.S. patent application Ser. No. 12/359,357 filed Jan. 26, 2009.

FIELD OF THE INVENTION

The present invention relates in general to a low profile surgical stapler for delivering multiple, large-sized staples to a body cavity through a small diameter delivery port and, in particular, to a feeding mechanism for advancing a stack of staples through a low profile delivery shaft of the stapler. The feeding mechanism moves a rigid body in and out of the staple stack during staple deployment to individually advance the staples through the delivery shaft and thereby reduce the potential for misalignment and jamming of the staples. This feeding mechanism may also be used for the feeding of other surgical fasteners including but not limited to ligating clips.

BACKGROUND OF THE INVENTION

Obesity is a medical condition affecting more than 30% of the population in the United States. Obesity affects an individual's quality of life and contributes significantly to morbidity and mortality. Surgical procedures have been developed for involuting the gastric cavity wall to reduce stomach volume as a treatment for obesity. In the gastric volume reduction (GVR) procedures (e.g., reduction gastroplasty, gastric plication, greater curvature plication, etc.), multiple pairs of suture anchoring devices, such as T-Tag anchors, are deployed through the gastric cavity wall. Preferably, the suture anchors are deployed through a small diameter port in a minimally invasive surgical procedure to reduce trauma to the patient. Following deployment of the T-Tag anchors, the suture attached to each individual pair of anchors is cinched to approximate the tissue, and secured to involute the cavity wall between the anchors. This procedure is described in greater detail in co-pending U.S. patent application Ser. Nos. 11/779,314 and 11/779,322, which are hereby incorporated herein by reference in their entirety. The GVR procedures described in these applications require individual placement of each suture anchor pair into the cavity wall tissue, and subsequent tensioning of the suture between the anchor pairs in order to involute the tissue.

The individual placement of the T-Tag anchors and manual suture tensioning is time intensive; increasing the duration, complexity and cost of the GVR procedure. To simplify and improve the GVR procedure, and to facilitate other small incision site surgical procedures within the peritoneal cavity, a stapler has been developed having a low-profile for use in small diameter (i.e. 5 mm or less) laparoscopic ports, a single trocar containing multiple small laparoscopic ports, or through a semi-rigid or flexible endoscopic platform (e.g., for use in natural orifice surgical procedures, single site laparoscopy, etc.). FIG. 1 illustrates an exemplary low profile stapler for use in GVR and other small incision site procedures in the peritoneal cavity including but not limited to reinforcement of staple lines (e.g., "oversewing" of a vertical sleeve gastrectomy), closing of surgical defects (e.g., gastrotomy closure), and fixation of temporary (e.g., liver retraction) or permanent (e.g., hernia mesh, gastric band securement) medical devices. As shown in FIG. 1, the stapler 10 includes a handle 12 having a pistol grip 14 shaped for grasping by a surgeon. A trigger assembly 16 is movably coupled to handle 12 to be drawn towards the pistol grip 14 during staple deployment. An elongated staple housing 20 having a longitudinal axis extends distally from handle 12. Housing 20 has sufficient length (on the order of 18") to enable use within an obese patient at numerous trocar access sites for traditional laparoscopic approaches. Likewise, housing 20 is sized to allow for passage through a small (3-5 mm) diameter trocar, although functional devices of a larger diameter are also possible without departing from the overall scope of the invention. A staple deploying assembly is at least partially disposed within the interior of housing 20 for discharging staples from a distal deployment opening 22. Trigger assembly 16 facilitates both the advancement of staples through housing 20, as well as the deployment of the staples from the distal opening 22

To obtain a large tissue purchase (which is desirable in GVR procedures) while using a small diameter delivery shaft, the stapler 10 deploys fasteners or staples having a folded, closed loop configuration. These closed loop or "box" staples have a small width in the initial, unformed condition. The width of the staple is expanded during opening and forming to allow the staple to obtain a large tissue purchase. FIG. 2 illustrates an exemplary box staple 30 for deployment from stapler 10. Staple 30 comprises a length of wire formed into a crown or back span 32 and first and second leg portions 34, 36 that intersect with opposite ends of the back span. The wire has a cylindrical cross-section, but may have other shapes (e.g., rectangular, elliptical, etc.) to provide optimal strength for the application or to aid in the feeding of the staples, and may or may not be uniform along the length of the wire. Leg portions 34, 36 intersect with back span 32 at an approximate angle α of 90° and extend in a substantially parallel fashion forward of the back span. Opposite back span 32, leg portions 34, 36 are bent inward to form staple end segments 40, 42. In a loop shape, two lengths of wire may be disposed across one side of the shape to enclose the shape, as demonstrated by the end segments 40, 42. Staple legs portions 34, 36 are bent at end segments 40, 42 to make one of the leg portions at least one wire diameter longer in length than the other leg portion. The longer length of one leg portion (i.e. staple leg 34 in FIG. 2) enables the end segments 40, 42 to lie in a common plane with back span 32. The tips of end segments 40, 42 are angled to form sharp prongs 46 for piercing tissue.

In stapler 10, a stack of the staples 30 is fed longitudinally through the housing in a plane parallel to the housing longitudinal axis. Within the staple stack, staples may be spaced apart from other staples, in contact with other staples, or alternate between states of contact and spaced. The staple stack preferably includes a large number of staples to facilitate procedures, such as GVR, which require a large number of tissue appositions or junctions. The staples are individually advanced outside of the open stapler end 22, and expanded open through actuation of the handle. After the staple pierces or otherwise engages the tissue sections to be joined, the stapler draws the expanded staple legs back inward to close the staple through the tissue. Box staples provide a number of advantages over previous surgical staple designs. These advantages include the ability to: use a smaller incision site, construct the staple from a stronger material, increase the work hardening in the formed staple through a greater number of bending points during formation, and feed the staples in a longitudinal rather than a vertical stack. Additional details regarding the closed loop staple design, as well as staple applicators, procedure applications, and methods of use are disclosed in co-pending U.S. patent application Ser. No. 12/359,351 filed Jan. 26, 2009 entitled "A SURGICAL STAPLER FOR APPLYING A LARGE STAPLE THROUGH A SMALL DELIVERY PORT AND A METHOD OF USING THE STAPLER TO SECURE A TISSUE FOLD", co-pending U.S. patent application Ser. No. 12/359,354 filed Jan. 26, 2009, entitled "A SURGICAL STAPLER FOR APPLYING A LARGE STAPLE THROUGH A SMALL DELIVERY PORT AND A METHOD OF USING THE STAPLER TO SECURE A TISSUE FOLD", co-pending U.S. patent application Ser. No. 12/359,357 filed Jan. 26, 2009 entitled "A SURGICAL STAPLER FOR APPLYING A LARGE STAPLE THROUGH A SMALL DELIVERY PORT AND A METHOD OF USING THE STAPLER TO SECURE A TISSUE FOLD", co-pending U.S. patent application Ser. No. 12/608,860 filed Oct. 29, 2009, entitled "BOX STAPLE METHOD WHILE KEEPING SAID BACK SPAN IN SUBSTANTIALLY ITS ORIGINAL SIZE AND SHAPE", and co-pending U.S. patent application Ser. No. 12/609,336 filed Oct. 30, 2009, entitled "A METHOD FOR APPLYING A SURGICAL STAPLE", which are hereby incorporated herein by reference in their entirety.

Despite the numerous advantages in using box staples, feeding a large number of the small staples through a relatively long delivery shaft can sometimes result in misalignment of the staples within the stack, causing the staples to jam prior to reaching the open stapler end. Jamming is particularly a concern when the staples are advanced through the delivery shaft by contact between the staples themselves, i.e. a driving force is applied to the end of the stack and transferred through the stack by each staple applying a force against the next previous staple in the stack in order to drive the full stack forward through the shaft. Previous stapler designs have reduced the potential for staple jamming by balancing loads between a number of flexible staple advancing and stopping components. However, this load balancing adds complexity and cost to the stapler.

Accordingly, to facilitate GVR and other procedures involving the fastening of layers of tissue within the peritoneal cavity, it is desirable to have a simplified, cost effective staple feeding mechanism for reliably feeding a large number of staples through a low profile stapler without misalignment and/or jamming of the staples. In particular, it is desirable to have a staple feeding mechanism for a low profile stapler which includes rigid, individual staple advancers for spreading the driving force of the mechanism through out the staple stack. Additionally, it is desirable to have a staple feeding mechanism in which the rigid staple advancers can be moved in and out of engagement with the staple stack during each staple deployment sequence. Doing so through a substantially rigid body motion (translation or rotation) of staple advancing components simplifies the staple feeding process and eases the strength and flexibility requirements for the staple advancing and stopping components by reducing the overall load requirements in the system. Further, it is desirable to have a staple feeding mechanism that advances the staple stack as part of the staple firing sequence without the need for separate actuation. Furthermore, it is desirable to have a staple feeding mechanism in which the staple driving member and controls are located within the staple housing rather than the handle. The present invention provides a staple feeding mechanism for a surgical stapler which achieves these objectives.

BRIEF DESCRIPTION OF THE DRAWINGS

FIG. 7A is an isometric view of a mid-section of the staple guide showing the feeding mechanism guide path in the inner surface of the guide;

FIG. 7B is a top view of the guide path shown in FIG. 7A;

FIG. 8 is a fragmentary, sectional view showing the distal and proximal ends of the rotating rod as the clamp begins moving distally;

FIG. 9 is a transverse, sectional view of the staple housing, taken at a point just distal of the control pin, showing the pin beginning to move distally in the guide path;

FIG. 10 is an isometric, fragmentary view of a portion of the staple feeding mechanism, showing the position of the control pin and staple advancers at an initial stage in the staple feeding sequence;

FIG. 11 is a top, partial view of the staple guide showing the control pin beginning to move distally within the guide path;

FIG. 12 is a fragmentary, sectional view showing the distal and proximal ends of the rotating rod as the rod rotates to bring the staple advancers inside the staple loops;

FIG. 13 is a transverse, sectional view of the staple housing, taken at a point just distal of the control pin, showing the pin pivoting within the guide path to rotate the staple advancers;

FIG. 14 is an isometric, fragmentary view of a portion of the staple feeding mechanism, showing the control pin rotating to place the staple advancers inside the staple loops;

FIG. 15 is a top, partial view of the staple guide showing the position of the control pin within the guide path as the pin begins to pivot with the path;

FIG. 16 is a fragmentary, sectional view showing the distal and proximal ends of the rotating rod as the staple advancers engage the staple end segments;

FIG. 17 is a transverse, sectional view of the staple housing, taken at a point just distal of the control pin, showing the pin advancing along the forward path as the clamp extension is drawn distally;

FIG. 18 is an isometric, fragmentary view of a portion of the staple feeding mechanism, showing the control pin rotated and advanced to place the staple advancers in contact with the staple end segments;

FIG. 19 is a top, partial view of the staple guide showing the position of the control pin as the pin advances through the forward path;

FIG. 20 is a fragmentary, sectional view showing the distal and proximal ends of the rotating rod as the staple advancers push the staple stack distally through the staple guide;

FIG. 21 is a transverse, sectional view of the staple housing, taken at a point just distal of the control pin, showing the pin further advanced along the forward path as the rotating rod moves distally with the clamp extension;

FIG. 22 is an isometric, fragmentary view of a portion of the staple feeding mechanism showing the control pin rotated to place the staple advancers inside the staple loops and the staple advancers advancing the staple stack distally;

FIG. 23 is a top, partial view of the staple guide showing the position of the control pin as the pin continues advancing through the forward path;

FIG. 26 is an isometric, fragmentary view of a portion of the staple feeding mechanism showing the control pin and staple advancers at the distal-most position in the staple feeding sequence;

FIG. 27 is a top, partial view of the staple guide showing the position of the control pin following dropping of the pin into the return path but prior to retraction of the pin;

FIG. 28 is a fragmentary, sectional view showing the distal and proximal ends of the rotating rod as the rod retracts proximally with the clamp extension at the end of the staple feeding sequence;

FIG. 29 is a transverse, sectional view of the staple housing, taken at a point just distal of the control pin, showing the pin rotated back to the initial angular position by the return path, and the pin following the return path back proximally at the conclusion of the feeding sequence;

FIG. 30 is an isometric, fragmentary view of a portion of the staple feeding mechanism, showing the staple advancers rotated away from the staple stack and retreating proximally at the conclusion of the staple feeding sequence;

FIG. 31 is a top, partial view of the staple guide showing the position of the control pin as the pin moves proximally through the return path;

DETAILED DESCRIPTION OF THE INVENTION

Figure 1:
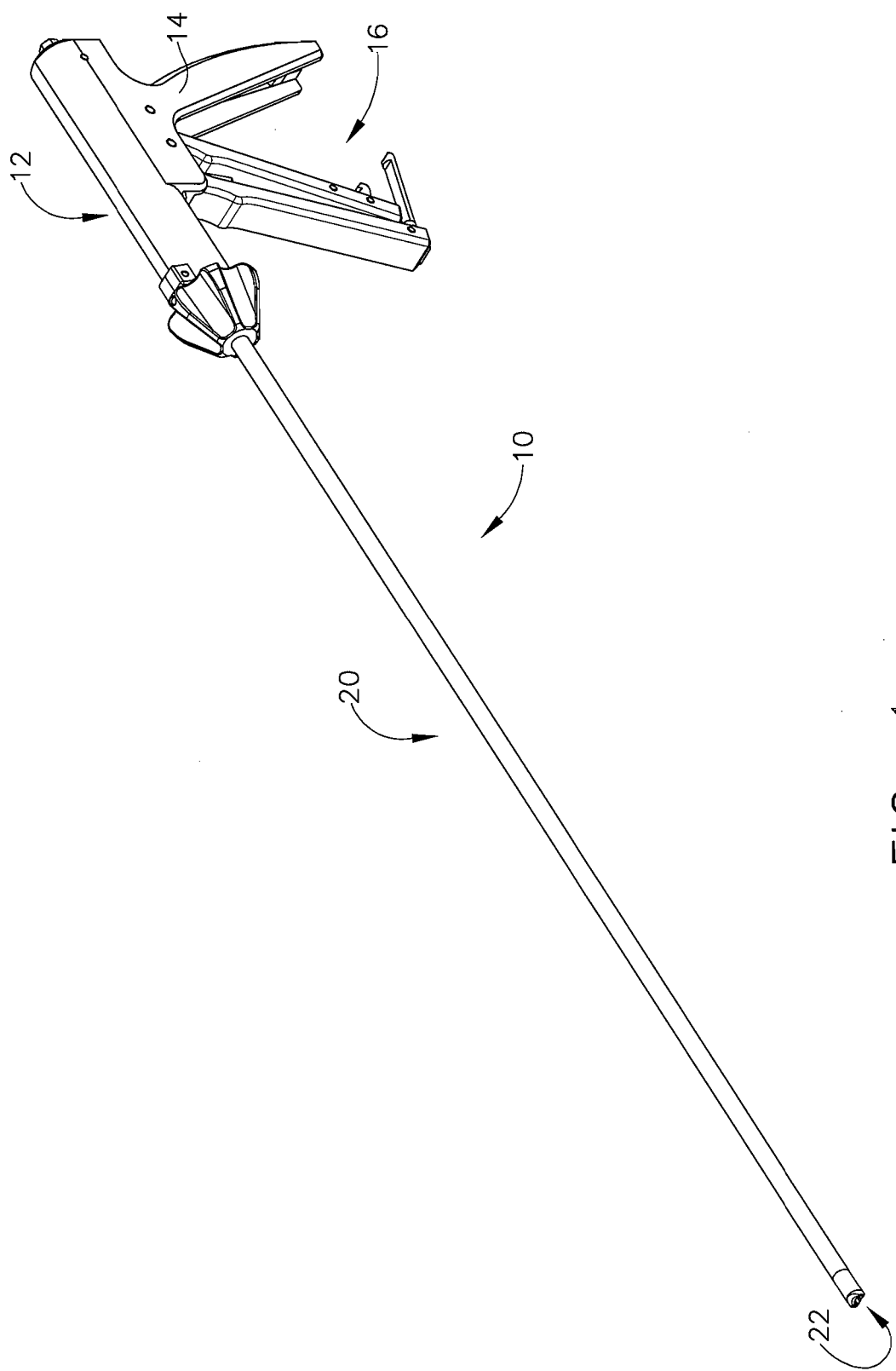
FIG. 1 is an isometric view of an exemplary low profile surgical stapler.
Figure 2:
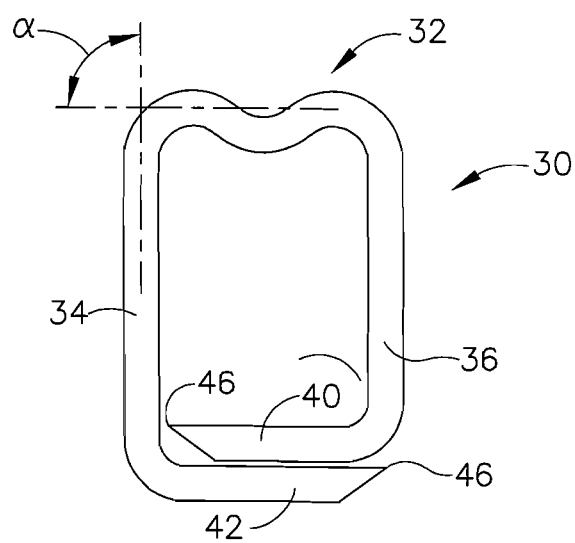
FIG. 2 is a top view of an exemplary box staple for deployment from the low profile stapler of FIG. 1.
Figure 3:
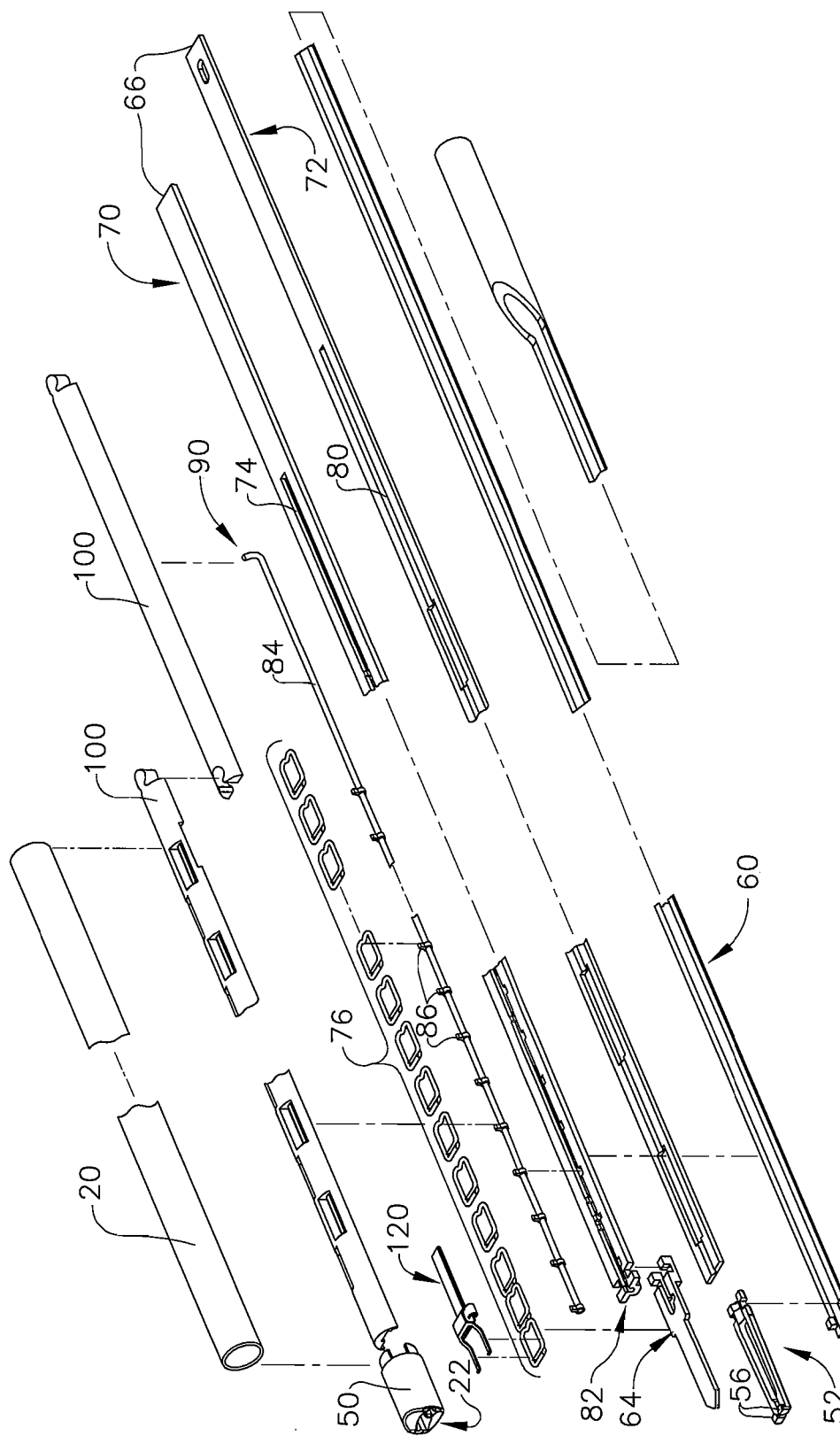
FIG. 3 is an exploded, isometric view of the distal end of the stapler of FIG. 1 incorporating a first embodiment of a staple feeding mechanism.

Referring again to the drawing figures, in which like numerals indicate like elements throughout the views, FIG. 3 shows the distal end of stapler 10 incorporating a first exemplary staple feeding mechanism of the present invention. As shown in FIG. 3, stapler 10 includes a staple former 50 which is attached to the distal end of staple housing 20. Staple deployment opening 22 is located at the distal end of former 50. Former 50 includes an inner channel (not shown) for conveying staples through the former and outside the stapler during deployment. Following passage of a staple outside opening 22, and the opening of the staple, former 50 advances over the opened staple to shape and close the staple through one or more tissue layers. Staples 30 are individually conveyed through former 50 and opening 22 by an anvil 52. Anvil 52 includes a pair of upwardly curved, staple holding tine 56 which hold onto the staple during passage through the former. The proximal end of anvil 52 is shaped for connecting the anvil to an anvil extension 60. Anvil extension 60 extends proximally from anvil 52 to a driving assembly in the handle.

A staple clamp 64 extends substantially along the surface of anvil 52. Clamp 64 comprises an elongated strip having substantially planar upper and lower surfaces and a width slightly narrower than the width of the unformed staples 30 to accommodate lateral shelves (not shown) for supporting the distal-most staple within the magazine channel. The lateral shelves are described in detail in previously incorporated U.S. patent application Ser. No. 12/608,860. Clamp 64 preferably has as small a length as necessary to cover the anvil 52. The distal end of clamp 64 is shaped for mating engagement with staple back span 32 for engaging and pushing the staple through former 50. The proximal end of clamp 64 is attached to a driving assembly in handle 12 via a clamp extension 66. Clamp extension 66 includes an upper section 70 and a lower section 72. Upper clamp extension 70 comprises an elongated, planar strip for supporting a staple stack 76. A longitudinally extending trough 74 is located midway across the width of the strip beneath staple stack 76. Trough 74 extends from the distal end of upper clamp extension 70 beyond the proximal end of staple stack 76. Lower clamp extension 72 is an elongated, rigid strip having a groove 80 in the surface adjoining upper clamp extension 70 to accommodate trough 74. Clamp 64 interconnects with the distal end of upper clamp extension 70 as indicated at 82.

Figure 4:
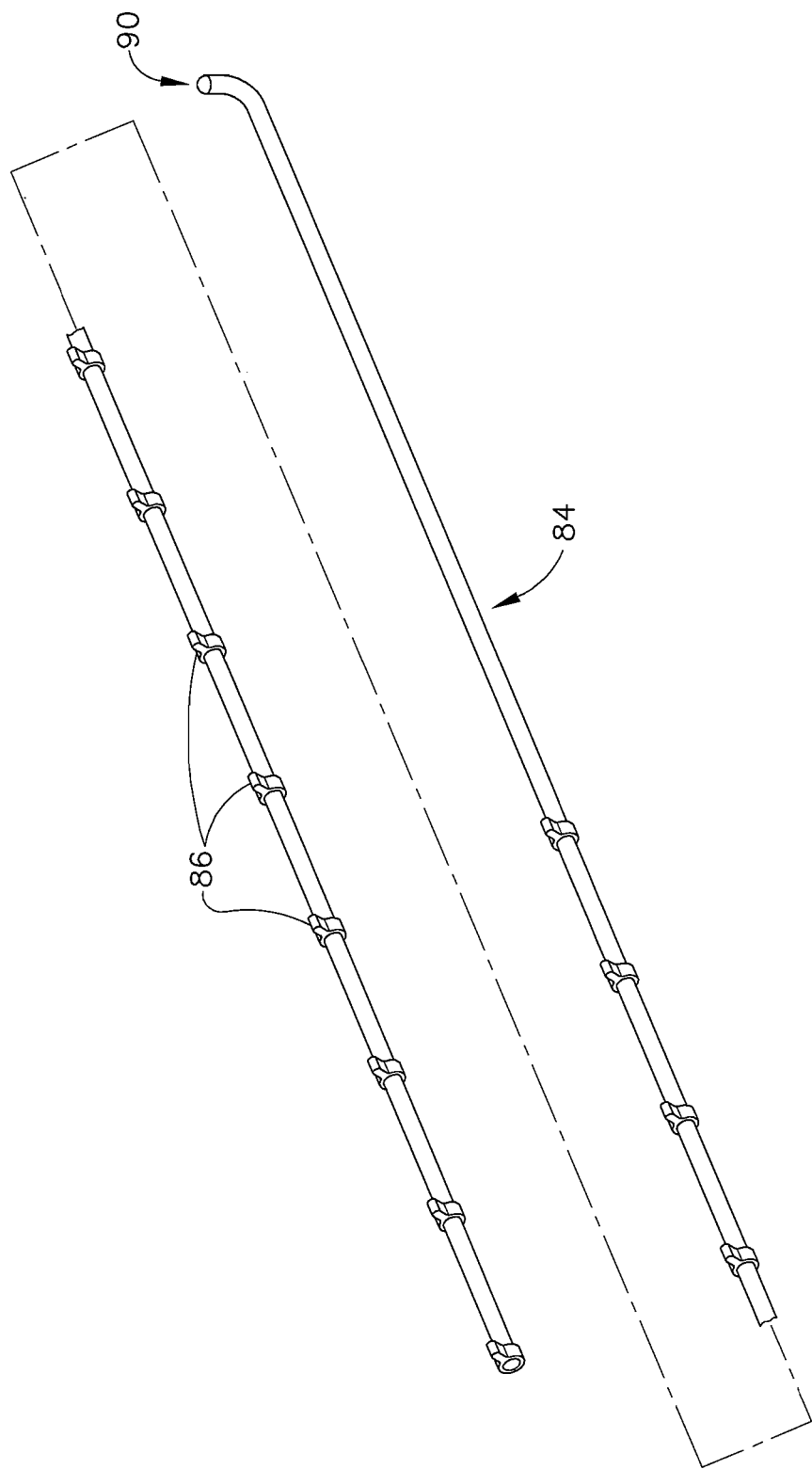
FIG. 4 is an isometric view of the rotating rod with staple advancers.

A staple driving member or actuator is provided within clamp extension trough 74 beneath the plane of staple stack 76. As shown in greater detail in FIG. 4, the actuator includes a rigid cylindrical shaft or rod 84 having a longitudinal axis substantially parallel to the longitudinal housing axis. A plurality of staple advancers 86 are evenly spaced apart substantially along the length of the rod. Staple advancers 86 comprise fins projecting out perpendicularly from the longitudinal rod axis. Staple advancers 86 extend along rod 84 to at least the proximal end of staple stack 76, to ensure that a staple advancer engages the proximal-most staple in the stack. Staple advancers 86 may be connected to rod 84 as shown or, alternatively, the rod and advancers may be formed as a single unitary piece. To form the rod and advancers as a single piece, a coining process is performed on the upper portion of the rod at the desired advancer locations. This coining process produces half-moon shaped protrusions of the rod material above the rod plane. In a further operation, each of the protrusions is machined, stamped, or otherwise modified to form a flat or squared-off, distal edge roughly perpendicular to the longitudinal rod axis. The resulting squared-off distal edge forms a staple contacting face for the advancer. The proximal end of rod 84 is curved at approximately a 90° angle relative to the longitudinal rod axis to form a control pin 90. Control pin 90 has a rounded tip for engaging a guide path as described below.

Figure 5:
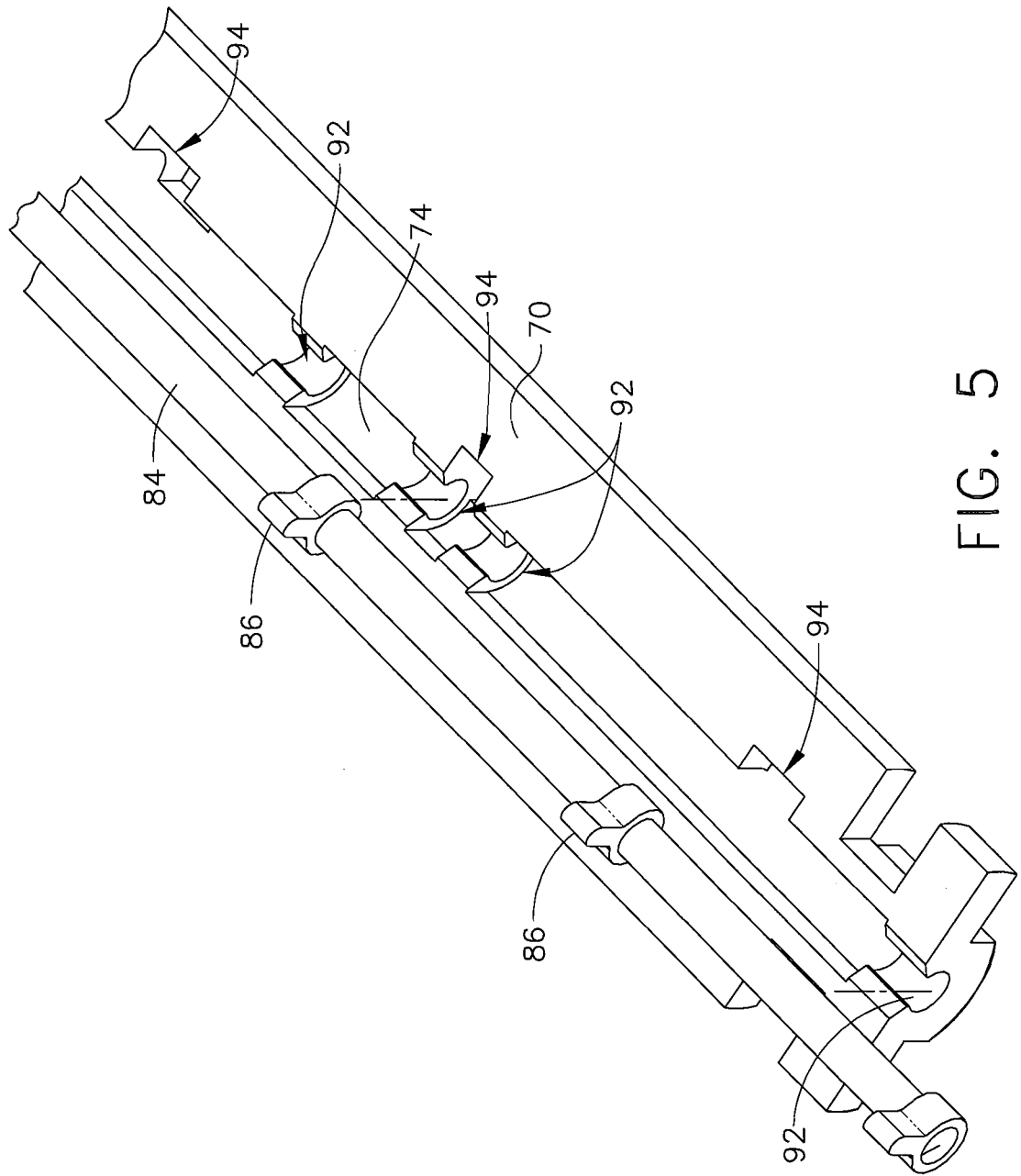
FIG. 5 is an isometric view of the distal end of the rotating rod and upper clamp extension.

As shown in FIG. 5, at least one retaining clip 92 is provided within trough 74 for retaining rod 84 in a rigidly spaced relationship from the staple stack 76. Rod 84 is snapped into the one or more clips 92 inside trough 74. Clips 92 retain rod 84 within trough 74 to translate the rod with clamp extension 66, while permitting the rod to rotate about the longitudinal rod axis. Upper clamp extension 70 also includes a plurality of notches 94 spaced apart along a side of trough 74. Notches 94 are aligned with staple advancers 86 to allow the advancers to rotate out of trough 74 and above the surface of the clamp extension. The distal end of rod 84 extends through an open distal end of trough 74 into clamp 64. The staple advancer 86 at the distal end of rod 84 is located in a groove in the proximal end of clamp 64. Rod 84 rotates relative to clamp 64 in the same manner as clamp extension 66, with the staple advancer extending up through a notch in the clamp. Rod 84 is fixed to upper clamp extension 70 by clips 92 to translate distally and then back proximally with the clamp extension during each staple deployment. Rod 84 and the attached staple advancers 86 are advanced and retracted by clamp extension 66 to index staple stack 76 distally approximately one staple length during each staple deployment.

Returning now to FIG. 3, a staple guide 100 is located proximal of former 50 inside staple housing 20. The outer perimeter of staple guide 100 is shaped to conform to the inner circumference of staple housing 20 to enable the staple guide to extend concentrically within the staple housing. Staple guide 100 is fixed at a proximal end to the stapler handle to prevent translation of the guide along the longitudinal housing axis during staple deployment. The connection between staple guide 100 and the handle 12, however, permits the staple guide to rotate with staple housing 20 about the longitudinal housing axis for positioning the staple prongs 46.

Figure 6:
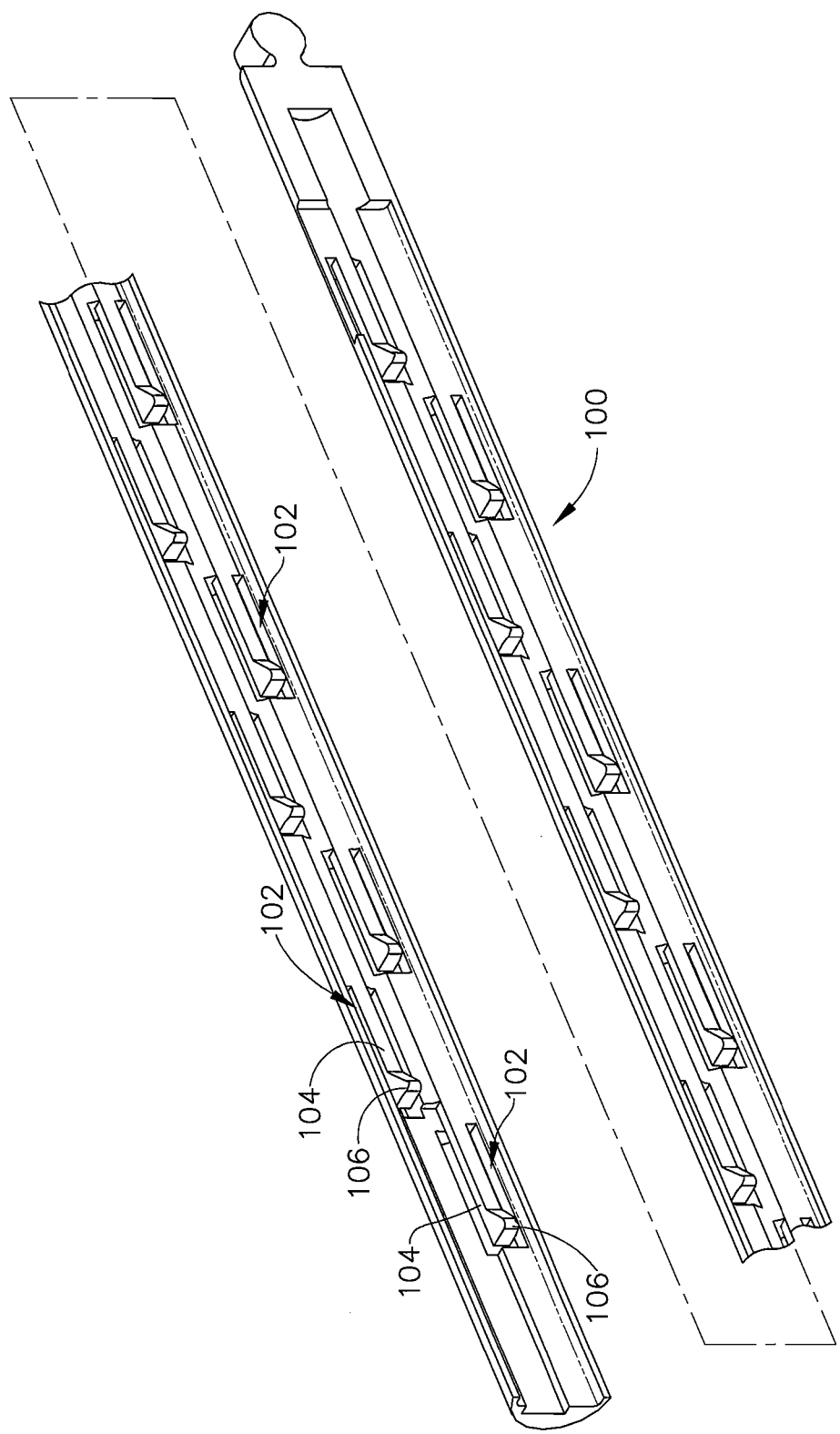
FIG. 6 is an isometric view of the distal end of the staple guide showing the anti-backup arms on the inner surface of the guide.
Figures 24, 25:
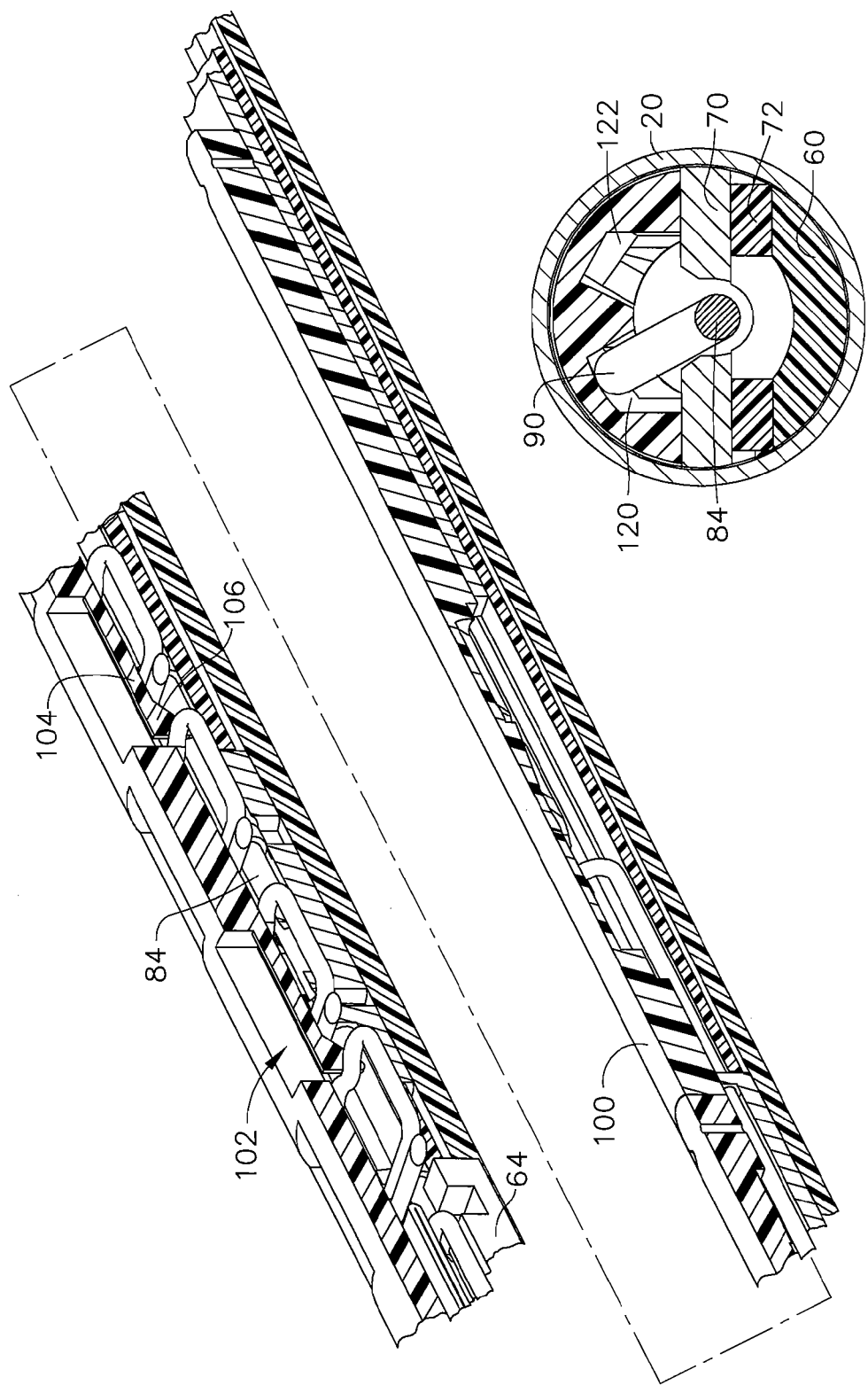
FIG. 24 is a fragmentary, sectional view showing the distal and proximal ends of the rotating rod as the rod reaches a distal-most position in the staple feeding sequence.
FIG. 25 is a transverse, sectional view of the staple housing, taken at a point just distal of the control pin, showing the control pin dropped into the return path.

As shown in FIG. 6, a plurality of longitudinally spaced openings 102 are formed into the inner surface of staple guide 100. An anti-backup arm 104 is connected at the proximal end of each opening 102 to extend distally substantially across the opening. Each anti-backup arm 104 includes an enlarged distal tip 106 which protrudes out in a direction perpendicular to the arm, beyond the surface of the staple guide 100. The distal side of each anti-backup arm tip 106 is substantially perpendicular to the arm to form a staple abutting face, while the proximal side of each arm tip 106 is tapered at approximately a 45° angle to form a staple deflecting face. Anti-backup arms 104 have a degree of flexibility relative to the inner surface of staple guide 100 to allow the arms to flex in and out of openings 102. Anti-backup arms 104 are spaced apart longitudinally along staple guide 100 a distance greater than or, at a minimum, substantially equal to, the length of staple legs 34, 36 in an unformed staple 30. It is conceived that uniform, larger distances between successive arms 104 could also be used to help increase device reliability, thereby allowing for part tolerances. Anti-backup arms 104 may be alternatively offset from the longitudinal centerline of staple guide 100, as shown.

A mechanism for rotating the staple actuator is located within the staple housing. As shown in FIGS. 7A and 7B, one possible location for the rotating mechanism is the inner surface of staple guide 100, however the rotating mechanism may also be located elsewhere in the staple housing. The rotating mechanism includes a closed, contoured guide path 112 proximal of anti-backup arms 104. Guide path 112 curves approximately 90° at two separate points along the path, as indicated at 114 and 116. Control pin 90 extends beyond the surface plane of clamp extension 66 into guide path 112 to be pivoted by the path as rod 84 translates distally and proximally during staple deployment. While control pin 90 traverses the guide path 112, the angular direction of the pin changes as the pin proceeds through curved path sections 114 and 116. The directional changes of control pin 90 rotate rod 84 within trough 74. As rod 84 rotates, staple advancers 86 are rotated from a position inside trough 74 to a position above the surface plane of clamp extension 66. Above clamp extension 66, the staple advancers 86 move up into the closed loops of the staples in stack 76. Guide path 112 comprises a forward path, indicated by arrow 120, in which control pin 90 pivots to rotate stapler advancers 86 up inside the loops of staples 30 and moves distally to advance the staples; and a return path, indicated by arrow 122, in which control pin 90 pivots to rotate the staple advancers down into trough 74 and moves proximally to retract the staple advancers beneath the staple stack back to the initial position. Elevation changes, indicated at 124 and 126, are located between the forward and return paths 120, 122 to transition control pin 90 between the paths. Rod 84 is comprised of a semi-rigid material to allow for some degree of flexing within the rod as the rod transitions between the forward and return paths. The interaction of control pin 90 with path 112 transforms the translational motion of the clamp extension into a rotation of the rod 84 in order to simultaneously translate and rotate the rod during the staple deployment sequence.

As mentioned above, a stack of staples 76 (shown in FIG. 3) extends longitudinally through housing 20 between staple guide 100 and upper clamp extension 70. Stack 76 extends in a plane parallel to the longitudinal axis of the staple housing. Staples 30 are conveyed within stack 76 to the distal end of stapler 10 prior to deployment. Within stack 76, each staple 30 is oriented such that the abutting end segments 40, 42 of the staple are positioned nearest the open stapler end 22. The back span 32 of the distal-most staple abuts the end segments 40, 42 of the second staple, while the back span of the second staple abuts the end segments of the third staple, and so forth through the length of the stack. The legs 34, 36 of each staple 30 are aligned substantially parallel to and may be in contact with the walls of staple guide 100 to maintain the forward orientation of the staples. Any number of staples 30 can be included within stack 76, with the preferred stapler embodiment capable of holding 20 or more staples. The individual staples within stack 76 may be visually differentiated to identify the position of the staples within the stack. Any optically detectable differentiation technique may be utilized including anodizing the staple material to produce staples of different colors. The distal end of staple stack 76 is conveyed along the surface of clamp 64 prior to the dropping of the individual staples onto anvil 52 for deployment.

Staple stack 76 is adjacent to the inner surface of staple guide 100 to enable the tips of anti-backup arms 104 to contact the staples within the stack. As shown in FIG. 8, the anti-backup arm tips 106 extend down between the back span 32 of a staple and the distal end segment 42 of the next adjacent staple prior to staple deployment. As the staple stack 76 is advanced distally by staple advancers 86, the end segments 40, 42 of the advancing staples contact the proximal, deflecting face of arm tips 106. As the staples advance against the deflecting faces, the staples gradually flex the anti-backup arms into staple guide openings 102, allowing the staples to pass beneath the arms. The straighter orientation of the distal tip faces, however, prevents the anti-backup arms 104 from flexing to allow the staples to retract. The distal, abutting face of arm tips 106 contact the back span 32 of each staple, particularly during retraction of the clamp and clamp extension following a staple deployment, to prevent staple stack 76 from moving proximally within staple housing 20.

Returning now to FIG. 3, a shoe 120 flexibly extends from the distal end of staple guide 100 for transferring staples from stack 76 onto anvil 52. Shoe 120 indexes the distal-most staple in stack 76 into a staging position on anvil 52 during each deployment sequence. The proximal end of shoe 120 is shaped to facilitate movement of staples beneath the shoe as the stack 76 is advanced through staple guide 100. The staple advancer 86 at the distal end of rod 84 (located within clamp 64) pushes the next staple in the stack under shoe 120 during each deployment cycle. Once a staple is under shoe 120, the shoe maintains the staple alignment until the staple is deposited over anvil tines 56. Shoe 120 may incorporate lateral shelves as described above.

At the beginning of the staple feeding sequence, control pin 90 is in a proximal-most position within forward guide path 120. With control pin 90 in this position, rod 84 is rotated to place staple advancers 86 down into clamp extension notches 94 and away from staple stack 76. Anti-backup arms 104 are in an initial position, with tips 106 down between the back span 32 and distal end segment 42 of each stacked staple. As trigger assembly 16 is squeezed to deploy a staple 30, a distally directed force is applied to clamp extension 66 by a driving assembly in the stapler handle. The driving force translates clamp extension 66 and attached rod 84 distally within housing 20. As mentioned above, staple guide 100 is fixed within the handle to remain stationary during staple deployment. The relative motion between the translating rod 84 and fixed staple guide 100 draws control pin 90 distally within the forward guide path 120, as shown in FIGS. 8-11. As control pin 90 continues to follow forward path 120 the angle of the path changes (as indicated at 114), causing the control pin to pivot with the path and, in turn, rotate rod 84, as shown in FIGS. 12-15. As rod 84 rotates, staple advancers 86 rotate above the surface of clamp extension 66 and into staple stack 76. Staple advancers 86 rotate to position each individual advancer inside the loop of a separate staple in the stack 76. Each staple advancer 86 rotates into a position proximal of the inner end segment 40 of the staple.

As control pin 90 finishes moving through angular path section 114, staple advancers 86 become fully rotated up to a position substantially perpendicular to the plane of staple stack 76. Continued distal movement of clamp extension 66 drives each staple advancer 86 forward within the respective staple loop towards the inner end segment 40, as shown in FIGS. 16-19. As staple advancers 86 move into contact with end segments 40, 42, the advancers individually push the staples in stack 76 forward within staple guide 100 towards the open stapler end 22. Contact between the staple stack 76 and the staples at the distal end of clamp 64 pushes the distal most staple in the stack forward into a staging position beneath shoe 120. As staples 30 advance, the distal end segments 42 of the staples apply a force against the proximal anti-backup tip faces 106. The pressure against the tapered, proximal tip faces flexes the anti-backup arms 104 into staple guide openings 102, allowing the staples to pass beneath the arms. Anti-backup arms 104 flex between a down position engaging the staple stack, and an up position within staple guide openings 102, to allow both the staple end segments 40, 42 and back span 32 to pass beneath the arms as the staple stack is indexed.

During the distal advance of clamp extension 66 and staple stack 76, control pin 90 continues moving distally through the forward path 120 in staple guide 100, as shown in FIGS. 20-23. As clamp extension 66 reaches a fully distal position, at the end of the trigger stroke, control pin 90 reaches the distal end of forward path 120, as shown in FIG. 24-27. Near the distal end of forward path 120, pin 90 changes elevation within the path (as indicated at 124), to drop the pin from the forward path into the return path 122. When clamp extension 66 reaches the distal-most point, staple advancers 86 have moved staples 30 a minimum distance of one staple length along the surface of the clamp and extension. The distal end of the staple stack 76 has been pushed forward on clamp 64 to place a new staple in the distal-most staging position beneath shoe 120. As staple stack 76 approaches the end of the forward advance, anti-backup arms 104 flex down proximal of the back span 32 of each stacked staple to prevent proximal movement of the staples.

Following deployment of a staple, the squeezing pressure on the trigger assembly is released, allowing the trigger assembly to pivot back open. As the trigger assembly pivots open, the driving assembly in the handle retracts clamp extension 66 back proximally to the initial position within staple housing 20. As clamp extension 66 retracts, the extension pulls rod 84 proximally, drawing control pin 90 back through return path 122. Control pin 90 rotates through angular path section 116 of return path 122 to rotate rod 84 and, in turn, staple advancers 86 down into notches 94 and out of engagement with the staple loops. After control pin 90 rotates back to the initial angular position, as shown in FIGS. 28-31, the pin continues to follow the return path 122 proximally as clamp extension 66 is retracted. As clamp extension 66 retracts, the distal, staple abutting faces of anti-backup arm tips 106 push against the back spans 32 of the individual staples 30. The contact between the abutting tip faces and staple back spans prevents staple stack 76 from retracting along with the clamp extension 66, thereby maintaining the indexed position of the staple stack. In an alternative embodiment, the anti-backup arm tips 106 push against end segment 40 of the staple to maintain the indexed positions of the staple stack.

As the trigger assembly reaches the fully open, initial position again, control pin 90 reaches the proximal end of return path 122. Near the proximal end of the return path, the elevation change in the path (indicated at 126) drops control pin 90 back into the forward path 120 in preparation for the next staple deployment. With pin 90 reset within guide path 112, staple advancers 86 are retracted back a full staple length and reset under the loop of the next proximal staple in the stack.

Figure 32:
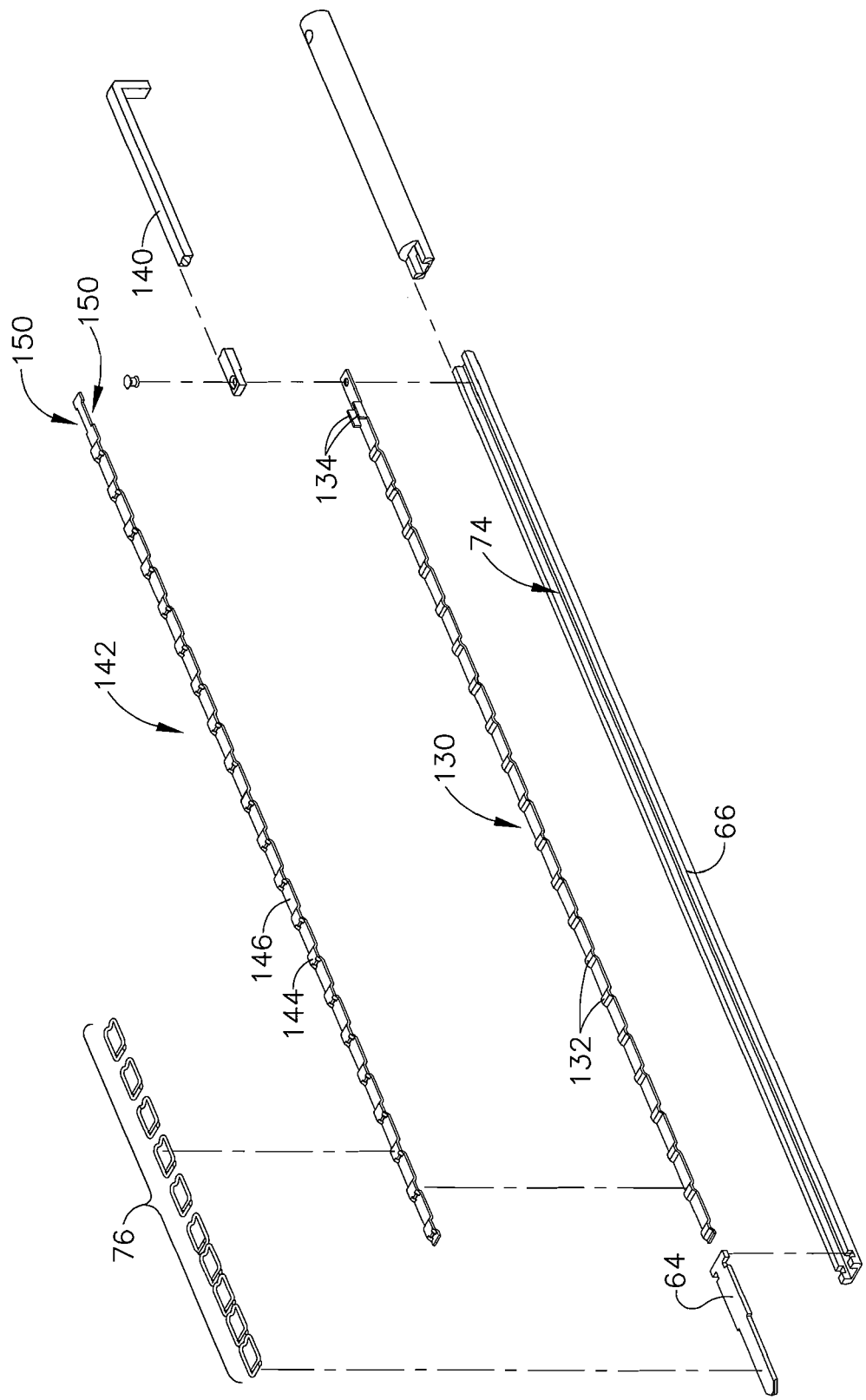
FIG. 32 is an exploded, isometric view of a second staple feeding mechanism embodiment.

Turning now to FIG. 32, which depicts an alternative staple feeding mechanism embodiment for stapler 10. In this embodiment, the staple driving member or actuator comprises an elongated cam shaft or ribbon 130 extending within clamp extension 66 and having a longitudinal axis substantially parallel to the longitudinal housing axis. Cam ribbon 130 has an undulating surface with raised ridges or lifters 132 evenly spaced apart substantially along the longitudinal axis of the ribbon. Cam ribbon 130 extends proximally from the connection between clamp 64 and clamp extension 66 and is rigidly spaced from staple stack 76 in a separate plane. A driving member 140 is connected to the proximal end of cam ribbon 130 for applying a force to the ribbon. During staple deployment, driving member 140 is translated by the trigger assembly, in turn translating cam ribbon 130 within staple housing 20. The proximal end of cam ribbon 130 includes parallel tabs 134 projecting from opposite sides of the ribbon. Tabs 134 extend up substantially perpendicular to the cam ribbon plane.

A feeder ribbon 142 extends longitudinally between the cam ribbon 130 and staple stack 76. Feeder ribbon 142 is substantially the same length as cam ribbon 130 and extends along the surface of the ribbon within clamp extension trough 74. Feeder ribbon 142 also has an uneven surface, with uniformly spaced staple advancers 144 elevated above the planar surface 146 of the ribbon. Staple advancers 144 extend across the width of the ribbon and have a longitudinal length that is less than staple legs 34, 36 but greater than the longitudinal length of cam ribbon lifters 132. During staple deployment, cam ribbon 130 is in communication with fastener advancers 144 to move the advancers into the staple loops and translate the staple stack 76 distally within the staple housing. Feeder ribbon 142 may be biased downward into clamp extension trough 74 by semi-flexible fins (not shown) extending laterally from the ribbon into the sides of the trough.

A pair of comparable length, parallel notches is formed in the sides of feeder ribbon 142 adjacent the proximal end of the ribbon. Notches 150 are sized to accommodate tabs 134 extending up from the surface of cam ribbon 130. Tabs 134 translate within notches 150 as cam ribbon 130 translates within clamp extension 66. At the distal and proximal ends of notches 150, tabs 134 push against the feeder ribbon 142 to drive the feeder ribbon in conjunction with the cam ribbon. Notches 150 have a greater longitudinal length than tabs 134, with the difference in length providing a dwell time between actuation of the cam ribbon 130 and actuation of the feeder ribbon 142. Feeder ribbon 142 is driven by contact with the cam ribbon tabs 134 rather than directly by a driving assembly in the handle. The difference in length between tabs 134 and notches 150 allows cam ribbon lifters 132 to translate in and out of longitudinal alignment with staple advancers 144 during the staple feeding sequence.

Figure 33:
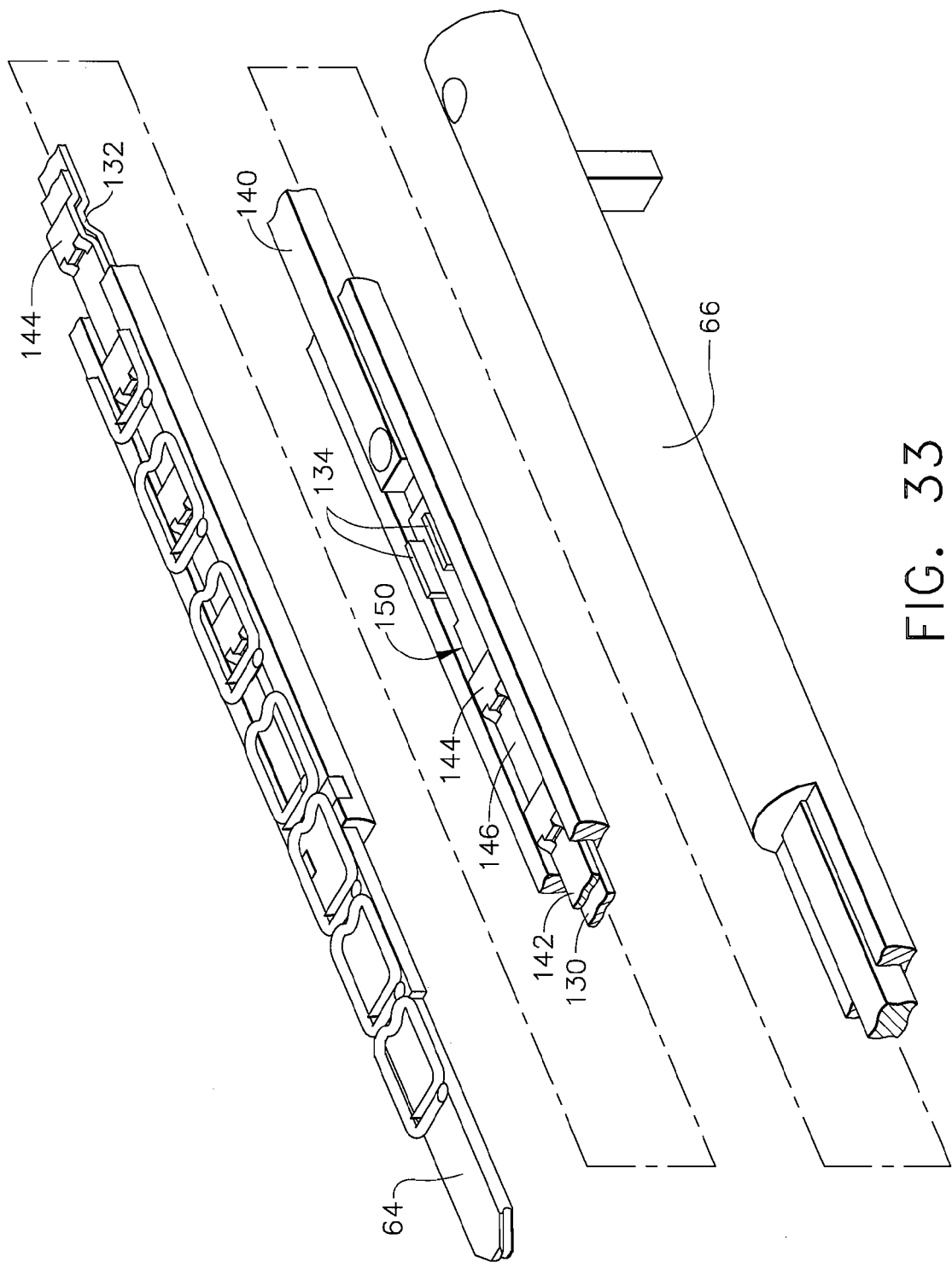
FIG. 33 is an isometric, fragmentary view of the staple feeding mechanism of FIG. 32, showing the feeding ribbon and cam ribbon in an initial position.
Figure 34:
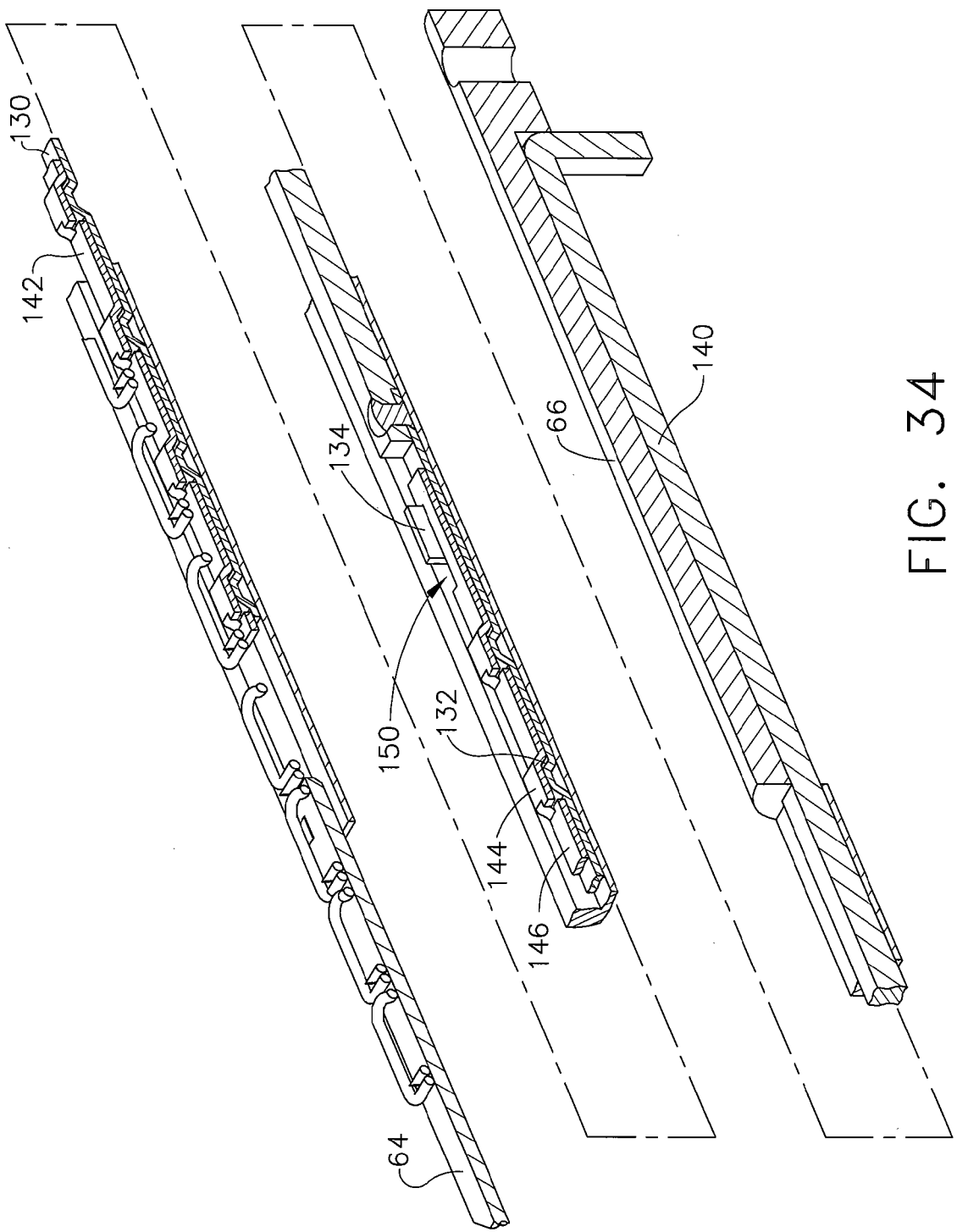
FIG. 34 is a fragmentary, sectional view of the second staple feeding mechanism embodiment in the initial position shown in FIG. 33.

FIGS. 33 and 34 show the initial position of the staple feeding mechanism prior to staple deployment. In this initial position, cam ribbon 130 and feeder ribbon 142 are both in a proximal-most position within clamp extension 66, with tabs 134 at the proximal end of notches 150. Cam lifters 132 are longitudinally aligned beneath staple advancers 144. With lifters 132 and staple advancers 144 aligned, feeder ribbon 142 is in a recessed position within clamp extension 66, and the staple advancers are below the plane of staple stack 76.

Figure 35:
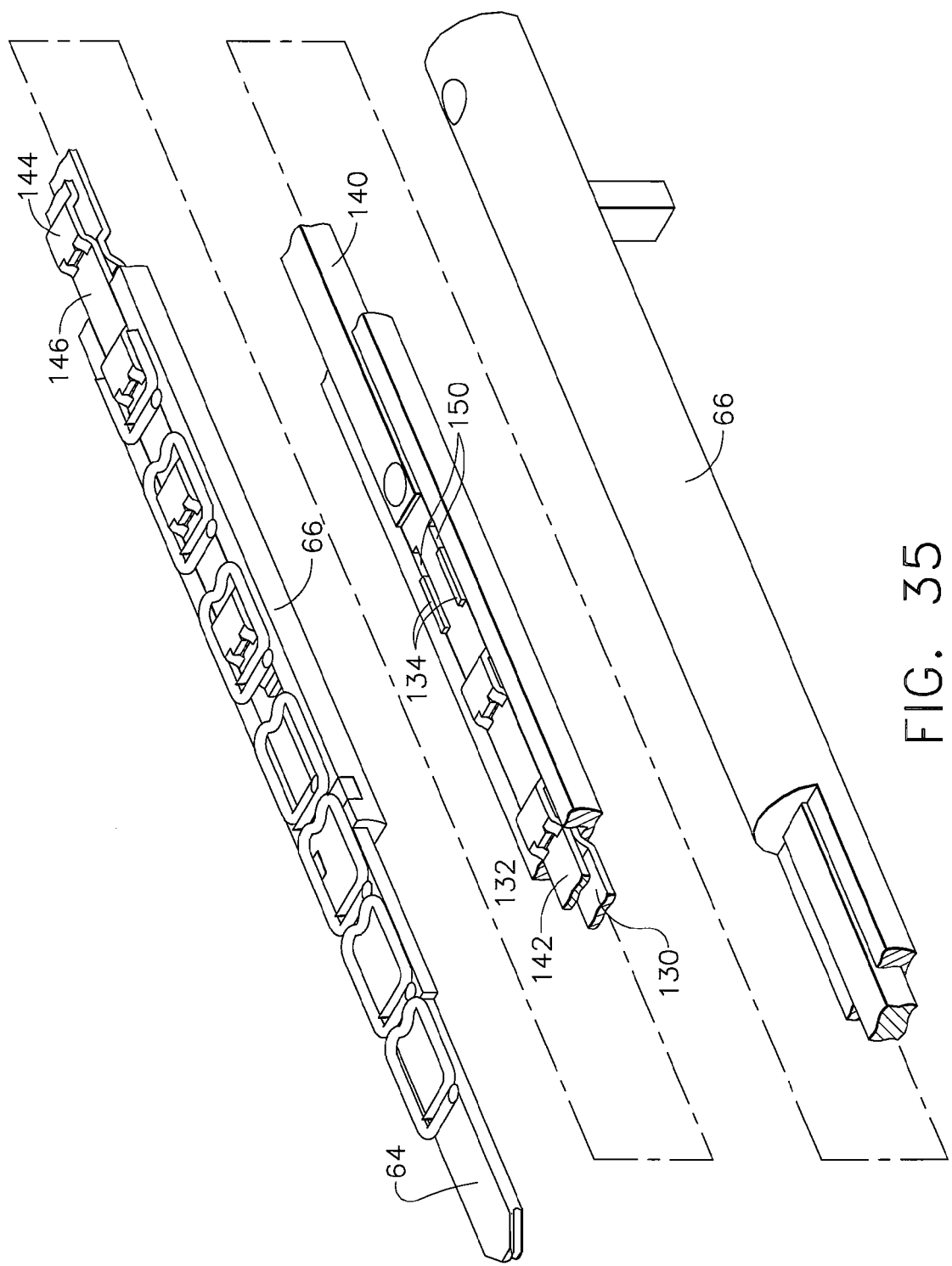
FIG. 35 is an isometric, fragmentary view of the staple feeding mechanism of FIG. 32, showing the cam ribbon advanced relative to the feeding ribbon at the beginning of the staple feeding sequence.
Figure 36:
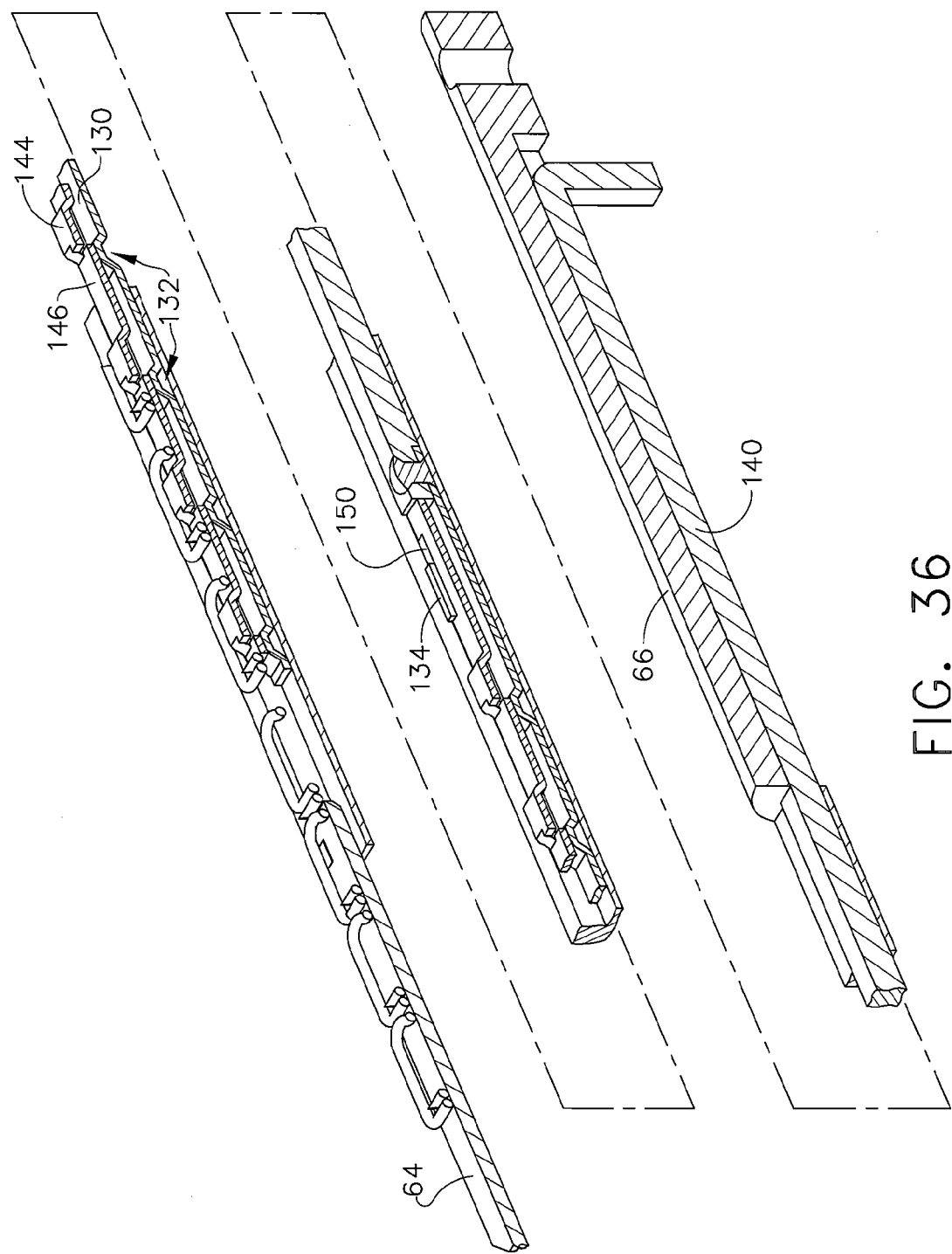
FIG. 36 is a fragmentary, sectional view of the second staple feeding mechanism embodiment showing the same feeding sequence position as FIG. 35.

As trigger assembly 16 is squeezed to deploy a staple 30, a distally directed force is applied to driving member 140 to advance the member and cam ribbon 130 distally within clamp extension 66. As cam ribbon 130 begins to move, feeder ribbon 142 remains stationary, as tabs 134 translate through notches 150. The relative movement between cam ribbon 130 and feeder ribbon 142 allows lifters 132 to move out of alignment with staple advancers 144 and ride underneath the planar feeder ribbon surface 146. As lifters 132 move underneath the planar surface of feeder ribbon 142, the lifters push the ribbon up within clamp trough 74. As feeder ribbon 142 lifts upward, staple advancers 144 move up inside the loops of the individual staples in stack 76. Feeder ribbon 142 remains stationary, allowing lifters 132 to translate under the ribbon, while tabs 134 progress through notches 150. Once tabs 134 reach the distal end of notches 150, as shown in FIGS. 35 and 36, the tabs apply a distally directed force to feeder ribbon 142. The force of the cam ribbon tabs 134 against feeder ribbon 142 pushes the feeder ribbon through the staple housing in unison with the cam ribbon. With staple advancers 144 raised into engagement with the staple stack 76, the distal movement of feeder ribbon 142 in turn causes each of the staple advancers to individually advance the engaged staple, thereby advancing the full staple stack along the upper surface of clamp extension 66. As the staple advancers on feed ribbon 142 translate staple stack 76, cam ribbon 130 remains rigidly spaced from the stack in a separate plane.

Figure 37:
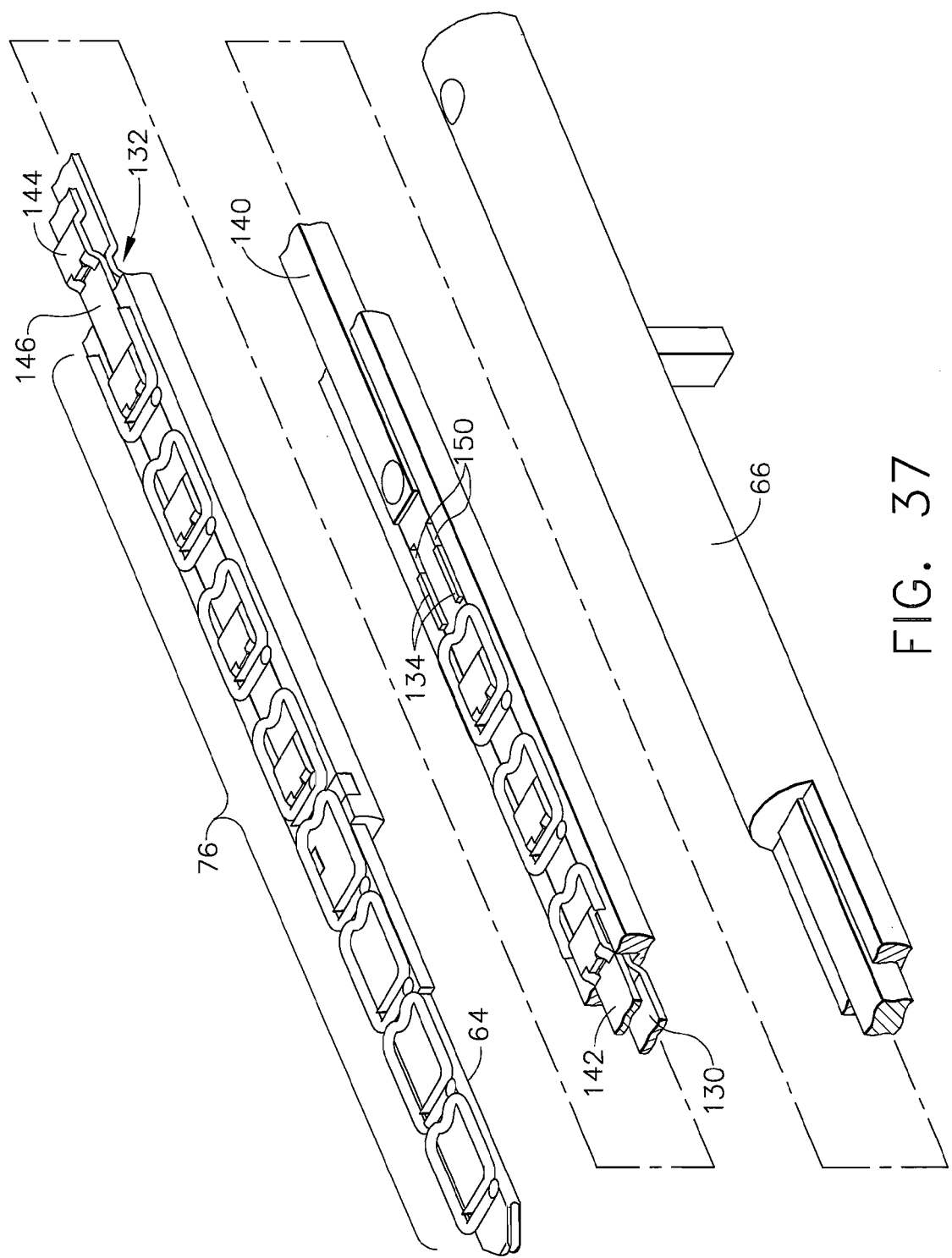
FIG. 37 is an isometric, fragmentary view of the staple feeding mechanism of FIG. 32, showing the cam ribbon advancing the feeding ribbon during the staple feeding sequence.
Figure 38:
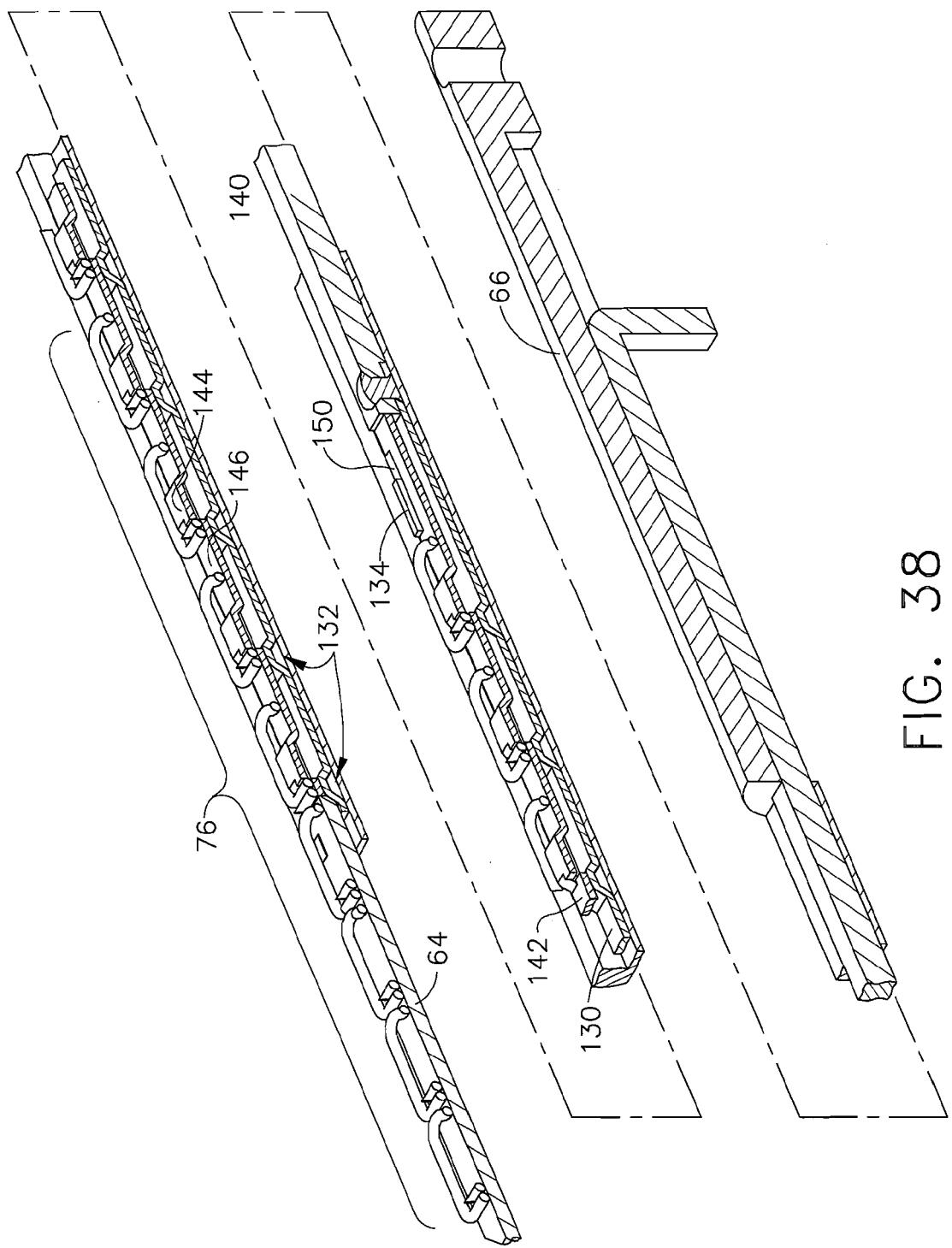
FIG. 38 is a fragmentary, sectional view of the second staple feeding mechanism embodiment in the same feeding sequence position shown in FIG. 37.
Figure 39:
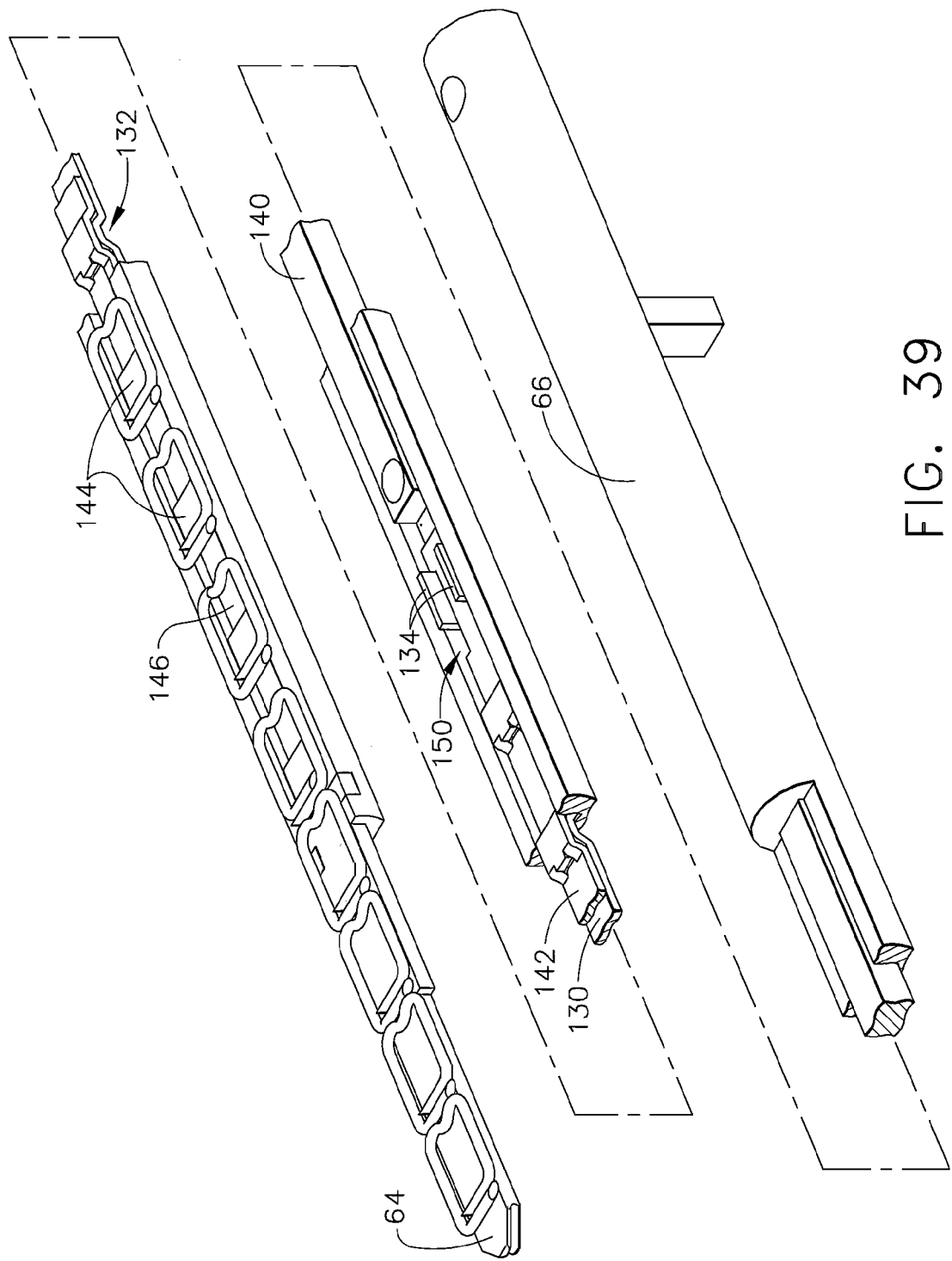
FIG. 39 is an isometric, fragmentary view of the staple feeding mechanism of FIG. 32, showing the cam and feeder ribbons retracted at the conclusion of the staple feeding sequence.
Figure 40:
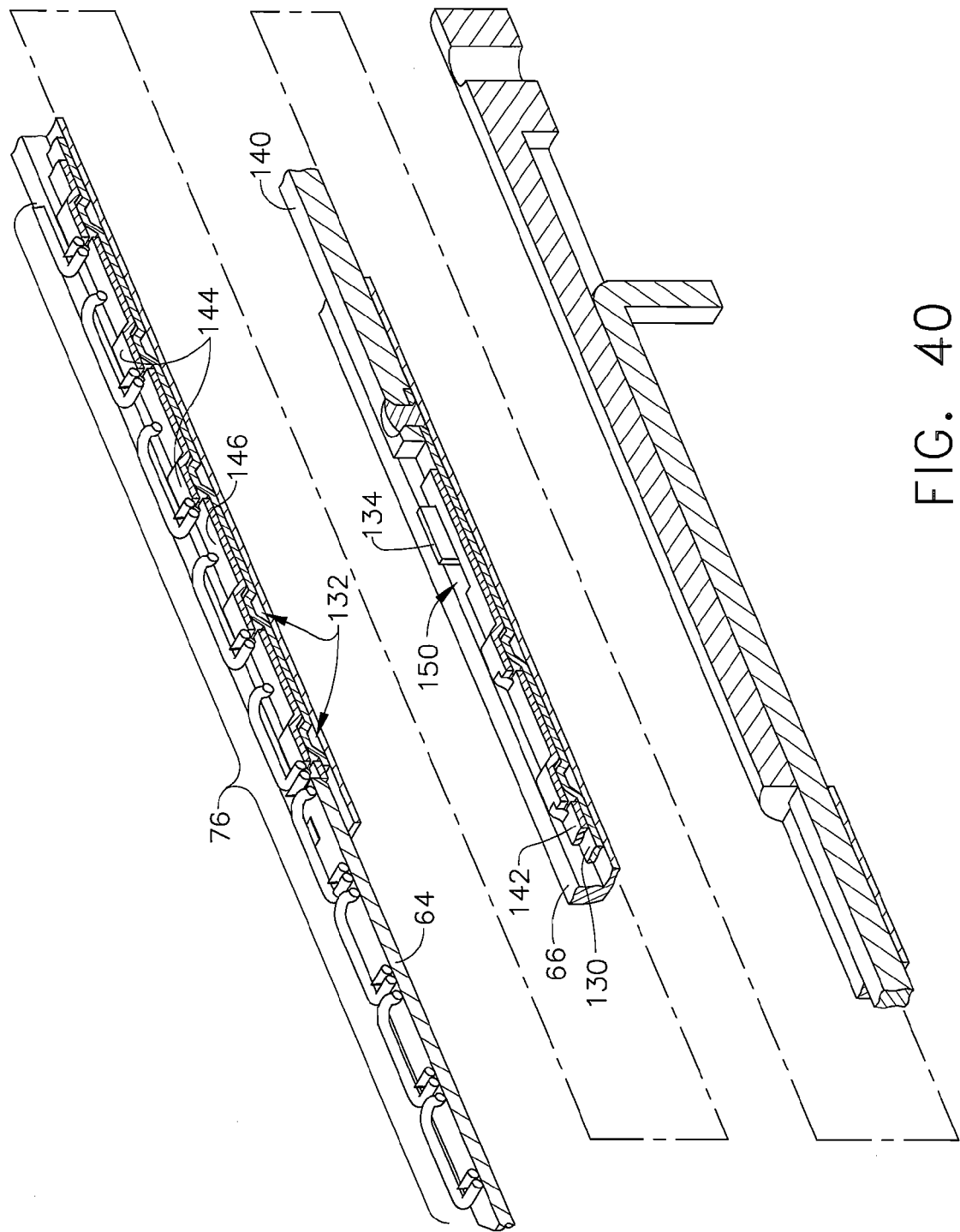
FIG. 40 is a fragmentary, sectional view of the second staple feeding mechanism embodiment showing the same position as FIG. 39.

At the end of the trigger stroke, staple advancers 144 have advanced the staple stack 76 one full staple length, as shown in FIGS. 37 and 38. As the trigger assembly pivots back open following staple formation, driving member 140 is pulled back proximally by the retracting trigger assembly. Driving member 140 in turn pulls cam ribbon 130 proximally due to the connection between the driving member and the ribbon. Cam ribbon 130 retracts ahead of feeder ribbon 142 due to the distal position of tabs 134 within notches 150. Retracting cam ribbon 130 ahead of feeder ribbon 142 allows staple advancers 144 to realign longitudinally with lifters 132 prior to moving proximally. The realignment of the lifters and staple advancers allows feeder ribbon 142 to fall back down inside clamp trough 74. Feeder ribbon 142 may drop down independently onto the retracting cam ribbon 130, or be pushed down by contact between the retracting staple advancers 144 and the staple crowns 32. In an alternative embodiment, feeder ribbon 142 is pushed down by semi-flexible fins as previously described. Staples 30 are held in the forward, indexed position as feeder ribbon 142 retracts by the anti-backup arms 104 described above. After tabs 134 retract to the proximal end of notches 150, as shown in FIGS. 39 and 40, the retracting cam ribbon 130 pulls feeder ribbon 142 proximally in unison with the cam ribbon. As the trigger assembly reaches a fully open position, the cam and feeder ribbons 130, 142 retract back to a reset condition, in which lifters 132 and staple advancers 144 are longitudinally aligned and located beneath the loop of the next proximal staple in stack 76. In this position, the cam and feeder ribbons are ready to again advance the staple stack during the next staple deployment.

The feeding mechanism described herein has been associated with a closed loop staple having at least partially overlapping end segments. Without departing from the scope of the current invention, other surgical fasteners, markers, or anchors that may require feeding in a stacked configuration may be used with this mechanism. A non-limiting list of candidate devices include staples of various geometries, hernia mesh anchors, T-Tags, and biopsy markers.

Any patent, publication, application or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The foregoing description of preferred embodiments of the invention has been presented for purposes of illustration and description. It is not intended to be exhaustive or to limit the invention to the precise form disclosed. Obvious modifications or variations are possible in light of the above teachings. The embodiments were chosen and described in order to best illustrate the principles of the invention and its practical application to thereby enable one of ordinary skill in the art to best utilize the invention in various embodiments and with various modifications as are suited to the particular use contemplated. It is intended that the scope of the invention be defined by the claims appended hereto.

What is claimed:

1. A surgical mechanism for feeding a fastener comprising:
   a. a housing having a longitudinal axis;
   b. at least one surgical fastener within said housing, said fastener comprising a crown and at least two legs extending therefrom, said surgical fastener disposed within said housing in a first plane parallel to said longitudinal axis;

c. an elongated actuator disposed within said housing, said actuator comprising a shaft substantially parallel to said longitudinal axis and rigidly spaced from said surgical fastener in a second plane;
d. said actuator comprising at least one radially extending advancer disposed along a length thereof; and
e. a mechanism for rotating said actuator so that said advancer engages said surgical fastener and rotating said actuator in an opposite direction so that said advancer disengages said surgical fastener.

2. The mechanism of claim 1 wherein said surgical fastener is substantially in the shape of a loop.

3. The mechanism of claim 1 wherein said actuator is located within said housing.

4. A surgical mechanism for feeding a fastener comprising:
a. a housing having a longitudinal axis;
b. at least one surgical fastener within said housing, said surgical fastener comprising a crown and at least two legs extending therefrom, said surgical fastener disposed within said housing in a first plane parallel to said longitudinal axis;
c. an elongated actuator disposed within said housing, said actuator rotatable and longitudinally movable within said housing, said actuator comprising a shaft substantially parallel to said longitudinal axis and rigidly spaced from said surgical fastener in a second plane;
d. said actuator comprising at least one radially extending advancer disposed along a length thereof; and
e. a mechanism for rotating said actuator so to engage said surgical fastener, and longitudinally moving said actuator to advance said surgical fastener.

* * * * *